(12) United States Patent
Peng et al.

(10) Patent No.: US 9,175,165 B2
(45) Date of Patent: Nov. 3, 2015

(54) CHEMOSENSORS FOR HYDROGEN SULFIDE

(75) Inventors: Hanjing Peng, Chamblee, GA (US); Binghe Wang, Marietta, GA (US)

(73) Assignee: Georgia State University Research Foundation, Inc., Atlanta, GA (US)

(*) Notice: Subject to any disclaimer, the term of this patent is extended or adjusted under 35 U.S.C. 154(b) by 22 days.

(21) Appl. No.: 13/997,963

(22) PCT Filed: Jan. 6, 2012

(86) PCT No.: PCT/US2012/020497
§ 371 (c)(1),
(2), (4) Date: Jun. 25, 2013

(87) PCT Pub. No.: WO2012/094603
PCT Pub. Date: Jul. 12, 2012

(65) Prior Publication Data
US 2013/0302904 A1    Nov. 14, 2013

Related U.S. Application Data

(60) Provisional application No. 61/430,390, filed on Jan. 6, 2011.

(51) Int. Cl.
| | | |
|---|---|---|
| G01N 33/00 | (2006.01) | |
| G01N 31/02 | (2006.01) | |
| G01N 31/00 | (2006.01) | |
| G01N 21/33 | (2006.01) | |
| C09B 56/20 | (2006.01) | |
| G01N 21/64 | (2006.01) | |
| G01N 31/22 | (2006.01) | |

(52) U.S. Cl.
CPC ............... *C09B 56/20* (2013.01); *G01N 21/64* (2013.01); *G01N 21/643* (2013.01); *G01N 31/22* (2013.01); *G01N 33/0044* (2013.01); *Y10T 436/184* (2015.01)

(58) Field of Classification Search
CPC ... G01N 33/0044; G01N 31/02; G01N 31/00; G01N 21/33; G01N 21/00; G01N 7/04; G01N 7/00
USPC ................................................. 436/120, 121
See application file for complete search history.

(56) References Cited

U.S. PATENT DOCUMENTS

2005/0215819 A1    9/2005    Williams

FOREIGN PATENT DOCUMENTS

CN    101302197    11/2008

OTHER PUBLICATIONS

Abe, et al., "A reduction-triggered fluorescence probe for sensing nucleic acids", Bioconjugate Chem., 19(6):1219-26 (2008).
Abe and Kimura, "The possible role of hydrogen sulfide as an endogenous neuromodulator", J. Neurosci., 16:1066-71 (1996).
Boehning and Snyder, "Novel neural modulators", Annu. Rev. Neurosci., 26:105-31(2003).
Choi, "Fluorimetric optode membrane for sulfide detection", Analyst, 123 (7):1631-4 (1998).
Culotta and Koshland, "NO news is good news", Science, 258:1862-5 (1992).
Goodwin, et al., "Determination of sulfide in brain tissue by gas dialysis/ion chromatography: postmortem studies and two case reports", J Anal. Toxicol., 13:105-9 (1989).
Hughes, et al., "Making and working with hydrogen sulfide: The chemistry and generation of hydrogen sulfide in vitro and its measurement in vivo: a review", Free Radical Bio.Med., 47:1346-53 (2009).
Jimenez, et al., "A new chromo-chemodosimeter selective for sulfide anion", J. Am. Chem. Soc., 125:9000-1 (2003).
Kazemi, et al., "Chemoselective reduction of azides with sodium sulfide hydrate umder solvent free conditions", Phosphorus, Sulfur, and Silicon, 179:1813-7 (2004).
Kimura, "Hydrogen sulfide as a neuromodulator", Mol. Neurobiol., 26:13-9 (2002).
Lefer, "A new gaseous signaling molecule emerges: cardioprotective role of hydrogen sulfide", PNAS, 104:17907-8 (2007).
Lei and Dasgupta, "Determination of Sulphide and mercaptans in caustic liquor", Anal. Chim. Acta., 226:165-70 (1989).
Li, et al., "Hydrogen sulfide is a novel mediator of lipopolysaccharide-induced inflammation in the mouse", FASEB J., 19:1196-8 (2005).
Martelli, et al., "Hydrogen sulphide: novel opportunity for drug discovery" Med. Res. Rev., (2011).
Moore, et al., "Hydrogen sulfide: from the smell of the past to the mediator of the future?" Trends Pharmacol. Sci., 24:609-11 (2003).
Morita, et al., "Smooth muscle cell-derived carbon monoxide is a regulator of vascular cGMP", PNAS, 92:1475-9 (1995).
Rodriguez-Fernandez, "Simple detector for oral malodour based on spectrofluorimetric measurements of hydrogen sulphide in mouth air", Analytica Chimica Acta, 398(1):23-31 (1999).
Savage and Gould, "Determination of sulfide in brain tissue and rumen fluid by ion-interaction reversed-phase high-performance liquid chromatography", J. Chromatogr. Biomed., 1990, 526:540-5 (1990).
Wang, "Two's company, three's a crowd: can H2S be the third endogenous gaseous transmitter", FASEB J., 16:1792-8 (2002).
Zhao, et al., "The vasorelaxant effect of H(2)S as a novel endogenous gaseous K(ATP) channel opener", EMBO J., 20:6008-16 (2001).

*Primary Examiner* — Christine T Mui
(74) *Attorney, Agent, or Firm* — Pabst Patent Group LLP

(57) ABSTRACT

Selective chemosensing agents for hydrogen sulfide are provided. The chemosensing agents can act fast under mild conditions, are chemically stable for long-term storage, are sensitive for detection under near physiological conditions, show a linear concentration-signal relationship within physiologically relevant hydrogen sulfide concentration ranges for easy quantitation, show minimal or no interference by other anions in the blood, and are functional in aqueous solutions and blood plasma.

19 Claims, 10 Drawing Sheets

CHEMOSENSORS FOR HYDROGEN SULFIDE

CROSS REFERENCE TO RELATED APPLICATIONS

This application is a 371 application published International Application No. PCT/2012/020497, entitled "Chemosensors for Hydrogen Sulfide", filed on Jan. 6, 2012, which claims priority to U.S. Ser. No. 61/430,390, filed Jan. 6, 2011, all of which are herein incorporated in their entirety by reference.

FIELD OF THE INVENTION

The invention is generally related to the field of chemosensors, more particularly to methods and compositions for detecting hydrogen sulfide.

BACKGROUND OF THE INVENTION

Traditionally, hydrogen sulfide ($H_2S$), well known for its unpleasant odor, was considered a toxic gas. However, recent studies have demonstrated that $H_2S$ is an endogenously produced gaseous signaling compound (gasotransmitter) with importance on par with that of the other two known endogenous gasotransmitters, nitric oxide (NO) (E. Culotta, D. E. Koshland, Science 1992, 258, 1862-1865) and carbon monoxide (CO) (T. Morita, M. A. Perrella, M. E. Lee, S. Kourembanas, P. Natl. Acad. Sci. U.S.A. 1995, 92, 1475-1479). Studies have indicated that $H_2S$ plays a regulatory role in the cardiovascular system (D. J. Lefer, P. Natl. Acad. Sci. U.S.A. 2007, 104, 17907-17908) by acting as a K-ATP channel opener (W. M. Zhao, J. Zhang, Y. J. Lu, R. Wang, EMBO J. 2001, 20, 6008-6016). $H_2S$ also functions as a modulator in the central nervous system (K. Abe, H. Kimura, J. Neurosci. 1996, 16, 1066-1071; D. Boehning, S. H. Snyder, Annu. Rev. Neurosci. 2003, 26, 105-131; H. Kimura, Mol. Neurobiol. 2002, 26, 13-19), respiratory system, gastrointestinal system, and endocrine system (A. Martelli, et al., Med. Res. Rev. 2011). These findings suggest that $H_2S$ exhibits many of the beneficial effects of NO without generating toxic reactive oxygen species (ROS). In fact, $H_2S$ acts as an anti-oxidant or scavenger of ROS. As a result, there has been a steady increase in the interest in understanding hydrogen sulfide's physiological and pathological functions (A. Martelli, et al., Med. Res. Rev. 2011; P. K. Moore, M. Bhatia, S. Moochhala, Trends Pharmacol. Sci. 2003, 24, 609-611; R. Wang, FASEB J. 2002, 16, 1792-1798).

Progress in studying the role of $H_2S$ in biological systems has been significantly limited by the lack of sensors and agents that allow for the rapid and accurate detection of $H_2S$. The standard method for sulfide analysis is a colorimetric assay based on the reaction between sulfide and N,N-dimethyl-p-phenylenediamine in the presence of $Fe^{3+}$ and hydrochloric acid (W. Lei, P. K. Dasgupta, Anal. Chim. Acta 1989, 226, 165-170; M. N. Hughes, M. N. Centelles, K. P. Moore, Free Radical Bio. Med. 2009, 47, 1346-1353). As shown below, the reaction produces methylene blue, a common dye which possesses a characteristic maximum absorption at 670 nm.

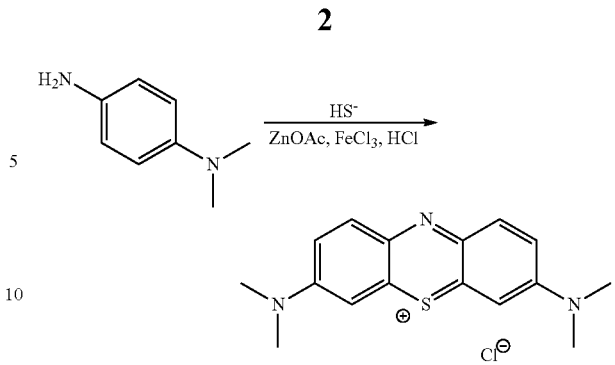

In practice, the colorometric assay involves the addition of zinc acetate, N,N-dimethyl-p-phenylenediamine dihydrochloride in 7.2 M HCl, and $FeCl_3$ in 1.2 M HCl to an aqueous sample containing an unknown quantity of sulfide. After incubation for 10 to 30 minutes, trichloroacetic acid is added to the reaction mixture. The sample is then centrifuged, and the absorption of methylene blue in the supernatant is measured using a spectrophotometer. The quantity of sulfide in the sample is determined by comparing the absorbance of the supernatant to a standard calibration curve.

While useful for some applications, this method of $H_2S$ detection possesses many intrinsic disadvantages. First, the assay requires a long reaction time (10-30 min), toxic reagents, and relatively harsh reaction conditions. In addition, the relationship between the absorption at 670 nm and the concentration of $H_2S$ is not linear due to the tendency for methylene blue to form dimers and trimers in solution (M. N. Hughes, M. N. Centelles, K. P. Moore, Free Radical Bio. Med. 2009, 47, 1346-1353).

An alternative colorimetric assay was developed by Martinez-Manez and co-workers (D. Jimenez, R. Martinez-Manez, F. Sancenon, J. V. Ros-L is, A. Benito, J. Soto, J. Am. Chem. Soc. 2003, 125, 9000-9001). This assay is based on a pyrylium-thiopyrylium transformation. Upon addition of sulfide in a water/acetonitrile (1:1) solution and further treatment with $H_2SO_4$, a dye containing an aniline-pyrylium backbone is transformed into a dye containing an aniline-thiopyrylium backbone. This transformation is accompanied by a large color change from magenta to blue.

While simple and easy to perform, the detection limit for this assay is only about 200 µM. For many applications, lower detection limits are required. For example, physiological concentrations of $H_2S$ are typically in the range of ~10-100 µM (J. C. Savage, D. H. Gould, J. Chromatogr. Biomed. 1990, 526, 540-545; L. R. Goodwin, et al., J Anal. Toxicol. 1989, 13, 105-109). As a result, the utility of this probe is limited.

Sensitive electrochemical methods for the detection of $H_2S$ have also been reported. However, these assays require sophisticated instrumentation and long equilibration times, greatly limiting their potential applications (M. N. Hughes, M. N. Centelles, K. P. Moore, Free Radical Bio. Med. 2009, 47, 1346-1353). For example, $H_2S$ catabolism is known to be rapid, resulting in $H_2S$ concentrations that continuously fluctuate in vivo. As a result, assays which require substantial equilibration times cannot be used as biosensors to measure $H_2S$ levels.

Therefore, there is a need for the development of new methods for the fast and selective detection of sulfide in biological systems. It is therefore an object of the invention to provide improved chemosensing agents for the detection and quantification of $H_2S$ in aqueous solution.

It is also an object of the invention to provide chemosensing agents for the detection and quantification of H$_2$S with lower detection limits and/or decreased equilibration time.

It is also an object of the invention to provide chemosensing agents for the detection and quantification of H$_2$S that do not require additional reagents, other than the chemosensing agent, to react with and/or stabilize H$_2$S.

It is a further object of the invention to provide methods of detecting sulfide in biological systems.

SUMMARY OF THE INVENTION

Chemosensing agents for the detection and/or quantification of H$_2$S are provided. The chemosensing agents contain one or more reactive functional groups covalently connected to a fluorophore. The reactive functional groups can be any moieties which undergo a chemical reaction in the presence of H$_2$S. The reactive functional groups and the fluorophore are covalently connected such that the reaction of the reactive function group with H$_2$S elicits one or more spectroscopically observable changes in the fluorophore's photophysical properties. Examples of spectroscopically observable changes include changes in absorption wavelength, changes in emission wavelength, changes in fluorescence lifetime, and changes in fluorescence quantum yield. Changes in fluorescence quantum yield can include a decrease in fluorescence intensity upon analyte exposure (termed "quenching") or an increase in fluorescence intensity upon analyte exposure. In preferred embodiments, the spectroscopically observable change is a change in the fluorescence of the chemosensing agent.

In certain embodiments, the chemosensing agent is designed to rapidly react with H$_2$S under physiological conditions, to be chemically stable for long-term storage, to exhibit a linear concentration-signal relationship within physiologically relevant H$_2$S concentration ranges, to exhibit minimal or no interference from other anions in the blood, to be functional in aqueous solutions, including blood and blood plasma, and combinations thereof. In some embodiments, the chemosensing agent reacts with H$_2$S in aqueous solution in the absence of additional reagents.

In some embodiments, the chemosensing agents possess detection limits for H$_2$S that are low enough to be used in biosensing applications. In preferred embodiments, the fluorescence assay possesses a detection limit of less than 100 μM, more preferably less than 50 μM, more preferably less than 25 μM, most preferably less than 10 μM.

In some embodiments, the chemosensing agents possess a short equilibration time upon exposure to H$_2$S. In preferred embodiments, the fluorescence intensity of the chemosensing agent, as measured at the maximum emission wavelength, reaches equilibrium less than ten minutes after contact with the H$_2$S, more preferably less than six minutes after contact with the H$_2$S, most preferably less than three minutes after contact with the H$_2$S.

In some embodiments, the chemosensing agent is not detectable or is weakly detectable prior to exposure of the chemosensing agent to H$_2$S; however, upon exposure to H$_2$S, the chemosensing agent forms a detectable species that can readily be measured by one or more analytical techniques known in the art. In certain embodiments, the chemosensing agent is non-fluorescent or weakly fluorescent prior to exposure of the chemosensing agent to H$_2$S; however, upon exposure to H$_2$S, the chemosensing agent forms a fluorescent species can readily be measured or observed. In particular embodiments, the chemosensing agent has a quantum yield of less than 0.05 prior to exposure of the chemosensing agent to H$_2$S, more preferably a quantum yield of less than 0.01 prior to exposure of the chemosensing agent to H$_2$S, more preferably a quantum yield of less than 0.005 prior to exposure of the chemosensing agent to H$_2$S; however, upon exposure to H$_2$S, the chemosensing agent forms a fluorescent species can readily be measured or observed.

In some embodiments, the chemosensing agent is represented by the following formula:

F—X—Y—RFG wherein

RFG represents an H$_2$S-reactive functional group;

Y is absent, or represents an activating group;

X is absent, or represents a spacer group; and

F is a fluorophore.

The reactive functional group can be any chemical moiety which reacts upon exposure to H$_2$S. In certain embodiments, the reactive functional group is a chemical moiety that is reduced upon exposure to H$_2$S. In preferred embodiments, the reactive functional group is an azido group that can be reduced by sulfide to form an amine.

The fluorophore can be a small molecule or a macromolecule. In some embodiments, the fluorophore is an organic or organometallic small molecule which contains one or more aromatic rings. In particular embodiments, the fluorophore is xanthene or a xanthene derivative, cyanine or a cyanine derivative, naphthalene or a naphthalene derivative, coumarin or a coumarin derivative; an oxadiazole derivative, pyrene or a pyrene derivative, an oxazine derivative, an acridine derivative, an arylmethine derivative, a tetrapyrrole derivative, or fluorene or a fluorene derivative. In some embodiments, the fluorophore is naphthalene or a naphthalene derivative, such as a dansyl or dansyl derivative or a naphthalimide or naphthalimide derivative.

The chemosensing agent can optionally contain an activating group that connects the reactive functional group and the fluorophore. When present, the activating group serves to influence the rate of reaction of the reactive functional group with H$_2$S. By increasing or decreasing the rate of reaction of the reactive functional group with H$_2$S, chemosensing agents with the desired reaction rate for particular sensing applications can be prepared.

In some embodiments, the rate of reaction, e.g., reduction, of the functional group may be too slow to be practical for the intended in vivo or in vitro applications. Therefore, the rate of reduction may be increased by introducing an activating group that increases the rate of reaction of the reactive functional group with H$_2$S. In certain embodiments, the activating group is an electron withdrawing group, such as a carbonyl group, sulfoxide group, or sulfonyl group.

The chemosensing agent can further contain a spacer group between the fluorophore and the activating group, if present, and the reactive functional group. When present, the spacer group should not significantly adversely affect the rate of reaction of the reactive functional group and/or the ability of the reaction product to be detected or measured.

In particular embodiments, the activating group is a sulfonyl group, the spacer group is absent, and the reactive functional group is an azide. In these embodiments, the chemosensing agent is represented by the following formula:

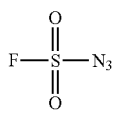

wherein F is a fluorophore as described above.

In certain embodiments, the chemosensing agent is defined by Formula I

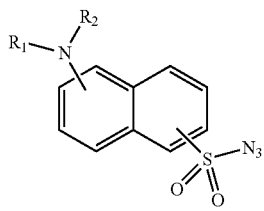

Formula I wherein

R$_1$ and R$_2$ are, independently, hydrogen, a substituted or unsubstituted alkyl group, a substituted or unsubstituted aryl group, or a substituted or unsubstituted heteroaryl group; or R$_1$ and R$_2$, together with the nitrogen atom to which they are attached, forms a 4- to 8-membered heterocyclic ring.

In certain embodiments, R$_1$ and R$_2$ are both methyl groups. In other embodiments, R$_1$ is a phenyl group and R$_2$ is hydrogen.

In certain embodiments, the chemosensing agent is one of the compounds shown below.

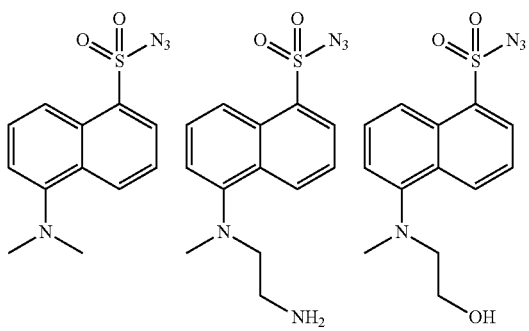

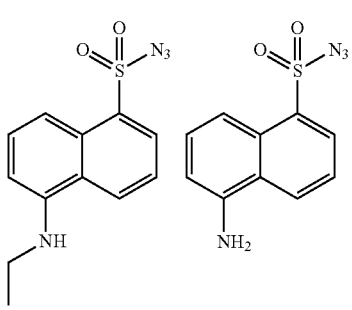

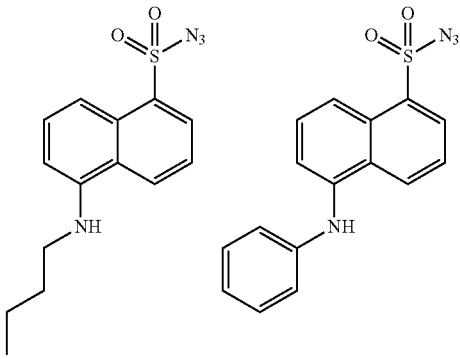

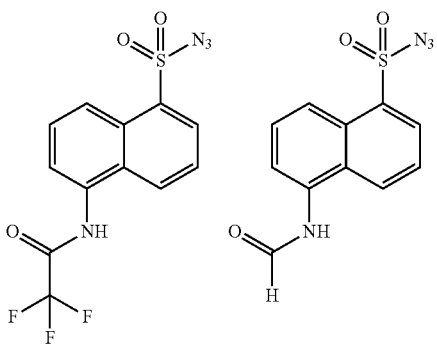

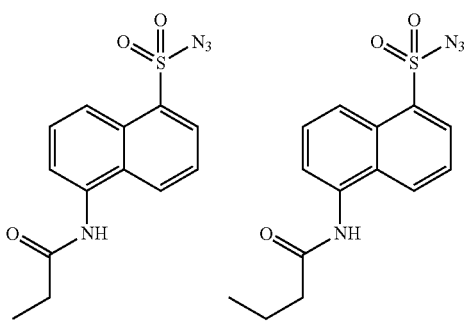

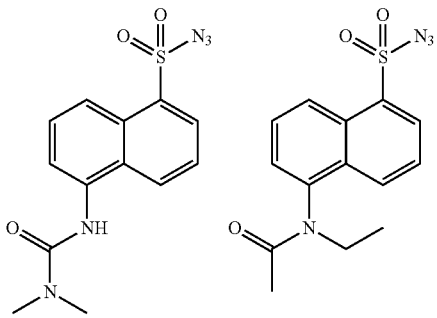

-continued

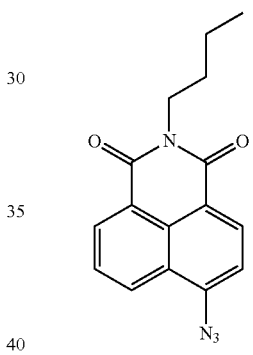

In certain embodiments, the chemosensing agent is defined by Formula II

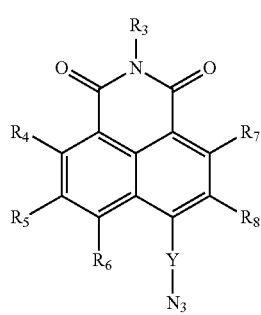

Formula II wherein
Y is absent, or represents an activating group;
$R_3$ is hydrogen, a substituted or unsubstituted alkyl group, a substituted or unsubstituted cycloalkyl group, a substituted or unsubstituted aryl group, a substituted or unsubstituted aralkyl group; a substituted or unsubstituted heterocyclyl group, or a substituted or unsubstituted heteroaryl group;

$R_4$-$R_8$ are, independently for each occurrence, hydrogen, a substituted or unsubstituted alkyl group, a substituted or unsubstituted aryl group, a substituted or unsubstituted aralkyl group, a substituted or unsubstituted heterocyclyl group, or a substituted or unsubstituted heteroaryl group, a halogen, a hydroxy group, a carbonyl group, such as a carboxyl, alkoxycarbonyl, formyl, or acyl group, a thiocarbonyl group, such as a thioester, thioacetate, or thioformate group, an alkoxy group, a phosphoryl group, a phosphate group, a phosphonate group, a phosphinate, an amino group, an amido group, an amidine group, an imine group, a cyano group, a nitro group, a sulfhydryl group, an alkylthio group, a sulfate group, a sulfonate group, a sulfamoyl group, a sulfonamide group, a sulfonyl group, a silyl group, or a trifluoromethyl group.

In certain embodiments, Y is absent, $R_3$ is a $C_1$-$C_{12}$ substituted or unsubstituted alkyl group, and $R_4$-$R_8$ are hydrogen.

In a particular embodiment, the chemosensing agent is defined by the structure shown below.

BRIEF DESCRIPTION OF THE DRAWINGS

FIG. 1 plots the fluorescence intensity (in arbitrary units) measured for DNS-Az alone (2, open bars, 100 μM, $\lambda_{Ex}$=340 nm, $\lambda_{Em}$=517 nm) and upon addition of 10 μM Na$_2$S (close bars, $\lambda_{Ex}$=340 nm, $\lambda_{Em}$=517 nm) in different solvent systems (left to right, deionized water, 20-100 mM sodium phosphate buffer (pH 7.5), 20 mM sodium phosphate buffer (pH 7.5) with 0.5% Tween-20, acetonitrile:water (1:1), water:sodium phosphate buffer (1:1), and acetonitrile).

DETAILED DESCRIPTION OF THE INVENTION

I. Definitions

Figure 1:
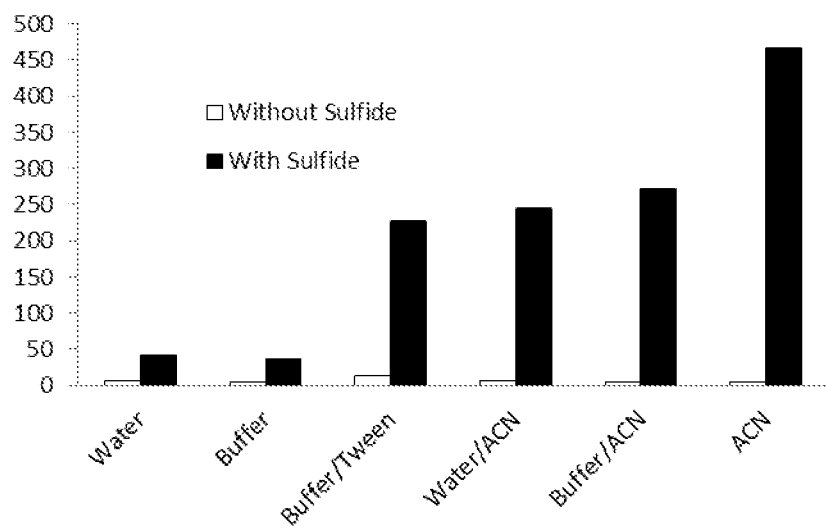
FIG. 1 is a bar graph showing the relative fluorescence response of the chemosensing agent DNS-Az (2) to sulfide.

"Azido Group" and "Azide" are used herein interchangeably, and refer to a functional group having the chemical formula shown below.

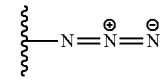

"Chemosensing Agent," as used herein, refers to a compound which exhibits a spectroscopically observable change in response to the presence of an analyte. Examples of spectroscopically observable changes include changes in absorption wavelength, changes in emission wavelength, changes in fluorescence lifetime, and changes in fluorescence quantum yield. Changes in fluorescence quantum yield can include a decrease in fluorescence intensity upon analyte exposure (termed "quenching") or an increase in fluorescence intensity upon analyte exposure. In preferred embodiments, the spectroscopically observable change is a change in the fluorescence of the chemosensing agent, such as a change in the emission wavelength, fluorescence lifetime, and/or quantum yield of the chemosensing agent.

"Electron-Withdrawing Group," as used herein, refers to an organic functional group that has the tendency to attract valence electrons from neighboring atoms in a molecule (i.e., the functional group is electronegative with respect to neighboring atoms). The relative electron-withdrawing capability of an organic functional group can be estimated from the group's Hammett constant (σ). See, for example, March, "Advanced Organic Chemistry," 5$^{th}$ Edition, 2001, Wiley-Interscience Publication, New York. The Hammett constant values are generally positive for electron withdrawing groups. Exemplary electron-withdrawing groups include nitro groups, acyl groups, formyl groups, sulfonyl groups, trifluoromethyl groups, and cyano groups.

"Fluorophore," as used herein, refers to a molecule or moiety, generally a polyaromatic hydrocarbon or heterocycle that has the ability to fluoresce. The ability to fluoresce, or "fluorescence", is generally understood to result from a three-stage process: (i) excitation, in which a photon is absorbed by the fluorophore, creating an excited electronic state in which the fluorophore has greater energy relative to the normal electronic state of the fluorophore; (ii) excited state lifetime (i.e., fluorescence lifetime), during which the fluorophore remains in the excited electronic state but also during which the energy of the state is partially dissipated; and (iii) emission, in which a photon of lower energy is emitted. Thus, a fluorophore absorbs a different wavelength of light (the "excitation wavelength" or "$\lambda_{Ex}$") than it emits (the "emission wavelength" or "$\lambda_{Em}$").

"Quantum Yield", as used herein, is a measurement of the efficiency of the fluorescence process, and is defined as the ratio of the number of photons emitted to the number of photons absorbed by the fluorophore. The fluorescence quantum yield of a fluorophore can be measured using standard methods known in the art. See, for example, Lakowicz, J. R. "Principles of Fluorescence Spectroscopy", $2^{nd}$ Ed., Plenum Press, New York, 1999.

"Fluorescence Assay," as used herein, refers to a chemical assay in which an analyte is identified, detected, and/or quantified by observing and/or measuring the fluorescence response of a chemosensing agent to the analyte.

"Fluorescence Analyzer," as used herein, refers to any machine, instrument, or device that can analyze and/or quantify the fluorescence emitted by a sample. Examples of fluorescence analyzers include fluorimeters, fluorescence microscopes, and flow cytometers.

"Small molecule," as used herein, refers to molecules with a molecular weight of less than about 2000 amu, more preferably less than about 1500 amu, most preferably less than about 1000 amu.

"Macromolecule," as used herein, refers to a large molecule, typically having a high relative molecular weight, such as a polymer, polysaccharide, protein, peptide, or nucleic acid. The macromolecule can be naturally occurring (i.e., a biomolecule) or can be prepared synthetically or semi-synthetically. In certain embodiments, macromolecules have a molecular weight of greater than about 1000 amu, more preferably greater than about 1500 amu, most preferably greater than about 2000 amu.

"Reactive Functional Group," as used herein, refers to a chemical moiety that undergoes a chemical reaction upon exposure to $H_2S$.

"Equilibration Time," as used herein, refers to the period of time from the point of mixing an analyte and a chemosensing agent to the point in time when the spectroscopically observable change being measured for the chemosensing agent no longer substantially changes.

"Detection Limit" and "Limit of Detection," as used herein, refer to the lowest concentration of an analyte that can be distinguished from the absence of the analyte (i.e., a blank control) with a stated confidence limit.

"Sample," as used herein, refers to a solid, liquid, or gas which may contain an analyte of interest, and is interrogated with a chemosensing agent for the purposes of determining the presence, absence, concentration, or combination thereof of the analyte of interest. In some embodiments, the solid, liquid, or gas is collected for the purposes of analyte detection. In preferred embodiments, the analyte is $H_2S$.

"Derivative," as used herein, refers to a compound which possesses the same conjugated core (i.e., delocalized pi-electron system) as a parent compound, but varies from the parent compound by a difference in one or more certain components. The derivative can differ from the parent compound, for example, in one or more substituents present on the conjugated core, which may include one or more atoms, functional groups, or substructures. In general, a derivative can be imagined to be formed, at least theoretically, from the parent compound via some chemical or physical process. For example, derivatives of naphthalene include naphthalene compounds possessing one or more substituents affixed to the naphthalene core.

The term "alkyl", as used herein, refers to the radical of saturated aliphatic groups, including straight-chain alkyl groups, branched-chain alkyl groups, cycloalkyl (alicyclic) groups, alkyl-substituted cycloalkyl groups, and cycloalkyl-substituted alkyl groups. In preferred embodiments, a straight chain or branched chain alkyl has 30 or fewer carbon atoms in its backbone (e.g., $C_1$-$C_{30}$ for straight chains, $C_3$-$C_{30}$ for branched chains), and more preferably 20 or fewer. Likewise, preferred cycloalkyls have from 3-10 carbon atoms in their ring structure, and more preferably have 5, 6 or 7 carbons in the ring structure. The term "alkyl" (or "lower alkyl") as used throughout the specification, examples, and claims is intended to include both "unsubstituted alkyls" and "substituted alkyls", the latter of which refers to alkyl moieties having one or more substituents replacing a hydrogen on one or more carbons of the hydrocarbon backbone. Such substituents include, but are not limited to, halogen, hydroxyl, carbonyl (such as a carboxyl, alkoxycarbonyl, formyl, or an acyl), thiocarbonyl (such as a thioester, a thioacetate, or a thioformate), alkoxyl, phosphoryl, phosphate, phosphonate, a phosphinate, amino, amido, amidine, imine, cyano, nitro, azido, sulfhydryl, alkylthio, sulfate, sulfonate, sulfamoyl, sulfonamido, sulfonyl, heterocyclyl, aralkyl, or an aromatic or heteroaromatic moiety.

Unless the number of carbons is otherwise specified, "lower alkyl" as used herein means an alkyl group, as defined above, but having from one to ten carbons, more preferably from one to six carbon atoms in its backbone structure. Likewise, "lower alkenyl" and "lower alkynyl" have similar chain lengths. Throughout the application, preferred alkyl groups are lower alkyls. In preferred embodiments, a substituent designated herein as alkyl is a lower alkyl group.

It will be understood by those skilled in the art that the moieties substituted on the hydrocarbon chain can themselves be substituted, if appropriate. For instance, the substituents of a substituted alkyl may include halogen, hydroxy, nitro, thiol, amino, azido, imino, amido, phosphoryl (including phosphonate and phosphinate), sulfonyl (including sulfate, sulfonamido, sulfamoyl and sulfonate), and silyl groups, as well as ethers, alkylthios, carbonyls (including ketones, aldehydes, carboxylates, and esters), —$CF_3$, —CN and the like. Cycloalkyls can be substituted in the same manner.

The terms "alkenyl" and "alkynyl" refer to unsaturated aliphatic groups analogous in length and possible substitution to the alkyls described above, but that contain at least one double or triple bond respectively.

"Aryl", as used herein, refers to 5-, 6- and 7-membered aromatic ring. The ring may be a carbocyclic, heterocyclic, fused carbocyclic, fused heterocyclic, bicarbocyclic, or biheterocyclic ring system, optionally substituted by halogens, alkyl-, alkenyl-, and alkynyl-groups. Broadly defined, "Ar", as used herein, includes 5-, 6- and 7-membered single-ring aromatic groups that may include from zero to four heteroatoms, for example, benzene, pyrrole, furan, thiophene, imidazole, oxazole, thiazole, triazole, pyrazole, pyridine, pyrazine, pyridazine and pyrimidine, and the like. Those aryl groups having heteroatoms in the ring structure may also be referred to as "heteroaryl", "aryl heterocycles", or "heteroaromatics". The aromatic ring can be substituted at one or more ring positions with such substituents as described above, for example, halogen, azide, alkyl, aralkyl, alkenyl, alkynyl, cycloalkyl, hydroxyl, alkoxyl, amino, nitro, sulfhydryl, imino, amido, phosphonate, phosphinate, carbonyl, carboxyl, silyl, ether, alkylthio, sulfonyl, sulfonamido, ketone, aldehyde, ester, heterocyclyl, aromatic or heteroaromatic moieties, —$CF_3$, —CN, or the like. The term "Ar" also includes polycyclic ring systems having two or more cyclic rings in which two or more carbons are common to two adjoining rings (the rings are "fused rings") wherein at least one of the rings is aromatic, e.g., the other cyclic rings can be cycloalkyls, cycloalkenyls, cycloalkynyls, aryls and/or heterocycles. Examples of heterocyclic ring include, but are not limited to, benzimidazolyl, benzofuranyl, benzothiofuranyl, benzothiophenyl, benzoxazolyl, benzoxazolinyl, benzthiazolyl, benztriazolyl, benztetrazolyl, benzisoxazolyl, benzisothiazolyl, benzimidazolinyl, carbazolyl, 4aH carbazolyl, carbolinyl, chromanyl, chromenyl, cinnolinyl, decahydroquinolinyl, 2H,6H-1,5,2-dithiazinyl, dihydrofuro[2,3 b]tetrahydrofuran, furanyl, furazanyl, imidazolidinyl, imidazolinyl, imidazolyl, 1H-indazolyl, indolenyl, indolinyl, indolizinyl, indolyl, 3H-indolyl, isatinoyl, isobenzofuranyl, isochromanyl, isoindazolyl, isoindolinyl, isoindolyl, isoquinolinyl, isothiazolyl, isoxazolyl, methylenedioxyphenyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxindolyl, pyrimidinyl, phenanthridinyl, phenanthrolinyl, phenazinyl, phenothiazinyl, phenoxathinyl, phenoxazinyl, phthalazinyl, piperazinyl, piperidinyl, piperidonyl, 4-piperidonyl, piperonyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydroquinolinyl, tetrazolyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl and xanthenyl.

"Alkylaryl", as used herein, refers to an alkyl group substituted with an aryl group (e.g., an aromatic or hetero aromatic group).

"Heterocycle" or "heterocyclic", as used herein, refers to a cyclic radical attached via a ring carbon or nitrogen of a monocyclic or bicyclic ring containing 3-10 ring atoms, and preferably from 5-6 ring atoms, consisting of carbon and one to four heteroatoms each selected from the group consisting of non-peroxide oxygen, sulfur, and N(Y) wherein Y is absent or is H, O, ($C_{1-4}$) alkyl, phenyl or benzyl, and optionally containing one or more double or triple bonds, and optionally substituted with one or more substituents. The term "heterocycle" also encompasses substituted and unsubstituted heteroaryl rings. Examples of heterocyclic ring include, but are not limited to, benzimidazolyl, benzofuranyl, benzothiofuranyl, benzothiophenyl, benzoxazolyl, benzoxazolinyl, benzthiazolyl, benztriazolyl, benztetrazolyl, benzisoxazolyl, benzisothiazolyl, benzimidazolinyl, carbazolyl, 4aH-carbazolyl, carbolinyl, chromanyl, chromenyl, cinnolinyl, decahydroquinolinyl, 2H,6H-1,5,2-dithiazinyl, dihydrofuro[2,3-b]tetrahydrofuran, furanyl, furazanyl, imidazolidinyl, imidazolinyl, imidazolyl, 1H-indazolyl, indolenyl, indolinyl, indolizinyl, indolyl, 3H-indolyl, isatinoyl, isobenzofuranyl, isochromanyl, isoindazolyl, isoindolinyl, isoindolyl, isoquinolinyl, isothiazolyl, isoxazolyl, methylenedioxyphenyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxindolyl, pyrimidinyl, phenanthridinyl, phenanthrolinyl, phenazinyl, phenothiazinyl, phenoxathinyl, phenoxazinyl, phthalazinyl, piperazinyl, piperidinyl, piperidonyl, 4-piperidonyl, piperonyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydroquinolinyl, tetrazolyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl and xanthenyl.

"Heteroaryl", as used herein, refers to a monocyclic aromatic ring containing five or six ring atoms consisting of carbon and 1, 2, 3, or 4 heteroatoms each selected from the group consisting of non-peroxide oxygen, sulfur, and N(Y) where Y is absent or is H, O, ($C_1$-$C_8$) alkyl, phenyl or benzyl. Non-limiting examples of heteroaryl groups include furyl, imidazolyl, triazolyl, triazinyl, oxazoyl, isoxazoyl, thiazolyl, isothiazoyl, pyrazolyl, pyrrolyl, pyrazinyl, tetrazolyl, pyridyl, (or its N-oxide), thienyl, pyrimidinyl (or its N-oxide), indolyl, isoquinolyl (or its N-oxide), quinolyl (or its N-oxide) and the like. The term "heteroaryl" can include radicals of an ortho-fused bicyclic heterocycle of about eight to ten ring atoms derived therefrom, particularly a benz-derivative or one derived by fusing a propylene, trimethylene, or tetramethylene diradical thereto. Examples of heteroaryl can be furyl, imidazolyl, triazolyl, triazinyl, oxazoyl, isoxazoyl, thiazolyl, isothiazoyl, pyraxolyl, pyrrolyl, pyrazinyl, tetrazolyl, pyridyl (or its N-oxide), thientyl, pyrimidinyl (or its N-oxide), indolyl, isoquinolyl (or its N-oxide), quinolyl (or its N-oxide), and the like.

"Substituted," as used herein, refers to all permissible substituents of the compounds described herein. In the broadest sense, the permissible substituents include acyclic and cyclic, branched and unbranched, carbocyclic and heterocyclic, aromatic and nonaromatic substituents of organic compounds. In certain embodiments, groups which are "substituted" contain between 1 and 5, more preferably between 1 and 4, most preferably between 1 and 3 substituents.

Illustrative substituents include, but are not limited to, halogens, hydroxyl groups, or any other organic groupings containing any number of carbon atoms, preferably 1-14 carbon atoms, and optionally include one or more heteroatoms such as oxygen, sulfur, or nitrogen grouping in linear, branched, or cyclic structural formats. Representative substituents include alkyl, substituted alkyl, alkenyl, substituted alkenyl, alkynyl, substituted alkynyl, phenyl, substituted phenyl, aryl, substituted aryl, heteroaryl, substituted heteroaryl, halo, hydroxyl, alkoxy, substituted alkoxy, phenoxy, substituted phenoxy, aroxy, substituted aroxy, alkylthio, substituted alkylthio, phenylthio, substituted phenylthio, arylthio, substituted arylthio, cyano, isocyano, substituted isocyano, carbonyl, substituted carbonyl, carboxyl, substituted carboxyl, amino, substituted amino, amido, substituted amido, sulfonyl, substituted sulfonyl, sulfonic acid, phosphoryl, substituted phosphoryl, phosphonyl, substituted phosphonyl, polyaryl, substituted polyaryl, $C_3$-$C_{20}$ cyclic, substituted $C_3$-$C_{20}$ cyclic, heterocyclic, substituted heterocyclic, aminoacid, peptide, and polypeptide groups.

Heteroatoms such as nitrogen may have hydrogen substituents and/or any permissible substituents of organic compounds described herein which satisfy the valences of the heteroatoms. It is understood that "substitution" or "substituted" includes the implicit proviso that such substitution is in accordance with permitted valence of the substituted atom and the substituent, and that the substitution results in a stable compound, i.e. a compound that does not spontaneously undergo transformation such as by rearrangement, cyclization, elimination, etc.

As used herein, the term "nitro" means —$NO_2$ and the term "sulfonyl" means —$SO_2$—.

II. Chemosensing Agents

Chemosensing agents are provided for the detection and quantification of $H_2S$. In the presence of $H_2S$, the chemosensing agents exhibit one or more spectroscopically observable changes which can be used to detect and/or quantify the $H_2S$.

Examples of spectroscopically observable changes include changes in absorption wavelength, changes in emission wavelength, changes in fluorescence lifetime, and changes in fluorescence quantum yield. Changes in fluorescence quantum yield can include a decrease in fluorescence intensity upon analyte exposure (termed "quenching") or an increase in fluorescence intensity upon analyte exposure. In preferred embodiments, the spectroscopically observable change is a change in the fluorescence of the chemosensing agent.

The chemosensing agents contain one or more reactive functional groups connected to a fluorophore. The reactive functional groups can be any moieties which undergo a chemical reaction in the presence of $H_2S$. The reactive functional groups and the fluorophore are covalently connected such that the reaction of the reactive function group with $H_2S$ elicits one or more spectroscopically observable changes in the fluorophore's photophysical properties.

In some embodiments, the chemosensing agent is not detectable or is weakly detectable prior to exposure of the chemosensing agent to $H_2S$. In these cases, upon exposure to $H_2S$, the chemosensing agent forms a detectable species that can readily be measured by one or more analytical techniques known in the art. In preferred embodiments, the fluorescence quantum yield of the chemosensing agent increases upon exposure to $H_2S$. In particular embodiments, the chemosensing agent is non-fluorescent or weakly fluorescent prior to exposure of the chemosensing agent to $H_2S$; however, upon exposure to $H_2S$, the chemosensing agent forms a fluorescent species can readily be measured by one or more analytical techniques known in the art.

In other embodiments, the chemosensing agent is spectroscopically detectable prior to exposure to $H_2S$. In these cases, exposure of the chemosensing agent to $H_2S$ preferably elicits one or more changes in the fluorescence of the chemosensing agent. The changes can include a decrease in the quantum yield of the chemosensing agent (i.e., quenching) upon exposure to $H_2S$, a shift in the maximum emission wavelength of the chemosensing agent to $H_2S$, a change in the shape of the emission spectra of the chemosensing agent to $H_2S$, a change in the fluorescence lifetime of the chemosensing agent upon exposure to $H_2S$, and combinations thereof. By observing and/or measuring one or more of these changes in fluorescence, $H_2S$ can be detected and quantified.

In some embodiments, the chemosensing agent is represented by the following formula:

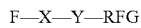

wherein
RFG represents a reactive functional group;
Y is absent, or represents an activating group;
X is absent, or represents a spacer group; and
F is a fluorophore.

In particular embodiments, the activating group is a sulfonyl group, the spacer group is absent, and the reactive functional group is an azide. In these embodiments, the chemosensing agent is represented by the following formula:

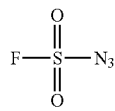

wherein F is a fluorophore.

In certain embodiments, the chemosensing agent is defined by Formula I

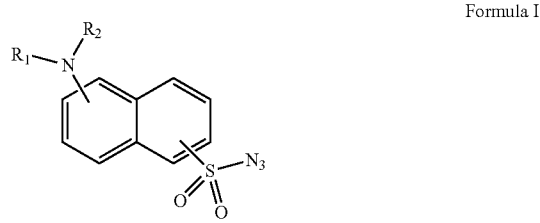

Formula I wherein $R_1$ and $R_2$ are, independently, hydrogen, a substituted or unsubstituted alkyl group, a substituted or unsubstituted aryl group, or a substituted or unsubstituted heteroaryl group; or $R_1$ and $R_2$, together with the nitrogen atom to which they are attached, forms a 4- to 8-membered heterocyclic ring.

In certain embodiments, $R_1$ and $R_2$ are both methyl groups. In other embodiments, $R_1$ is a phenyl group and $R_2$ is hydrogen.

In certain embodiments, the chemosensing agent is one of the compounds shown below.

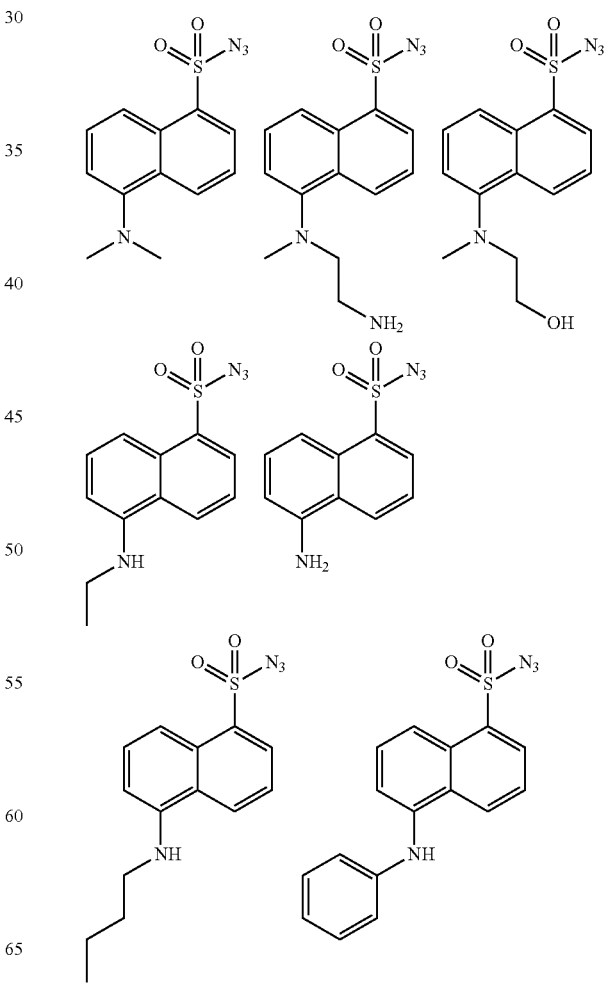

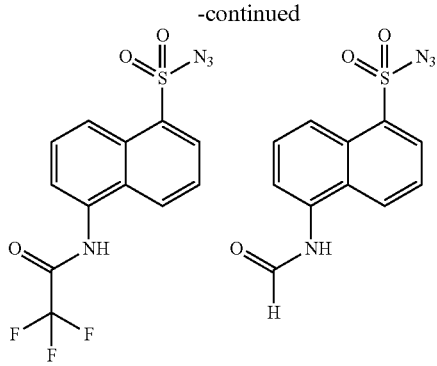

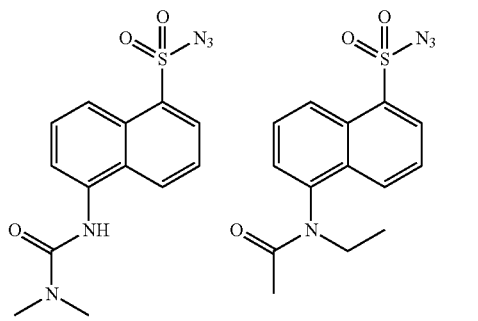

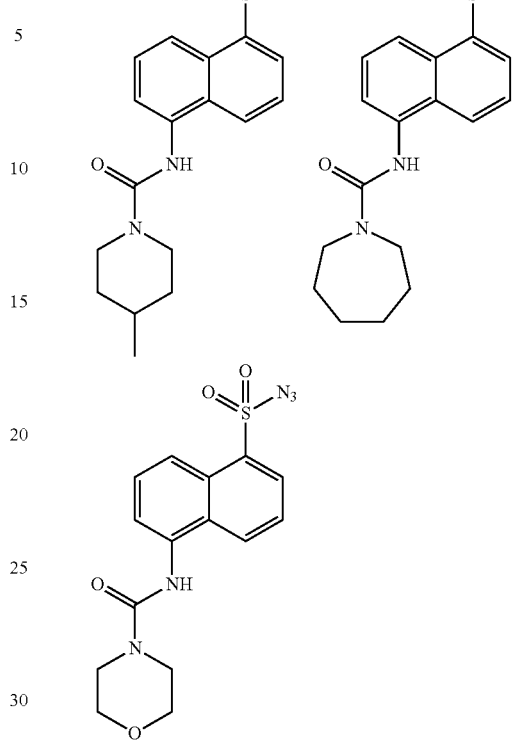

In certain embodiments, the chemosensing agent is defined by Formula II

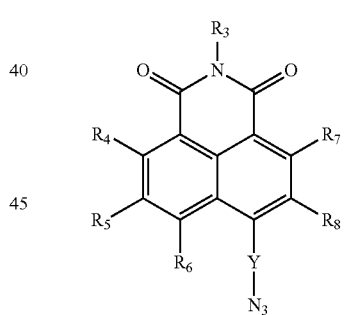

Formula II wherein

Y is absent, or represents an activating group;

$R_3$ is hydrogen, a substituted or unsubstituted alkyl group, a substituted or unsubstituted cycloalkyl group, a substituted or unsubstituted aryl group, a substituted or unsubstituted aralkyl group; a substituted or unsubstituted heterocyclyl group, or a substituted or unsubstituted heteroaryl group;

$R_4$-$R_8$ are, independently for each occurrence, hydrogen, a substituted or unsubstituted alkyl group, a substituted or unsubstituted aryl group, a substituted or unsubstituted aralkyl group, a substituted or unsubstituted heterocyclyl group, or a substituted or unsubstituted heteroaryl group, a halogen, a hydroxy group, a carbonyl group, such as a carboxyl, alkoxycarbonyl, formyl, or acyl group, a thiocarbonyl group, such as a thioester, thioacetate, or thioformate group, an alkoxy group, a phosphoryl group, a phosphate group, a phosphonate group, a phosphinate, an amino group, an amido group, an amidine group, an imine group, a cyano group, a nitro group, a sulfhydryl group, an alkylthio group, a sulfate group, a sulfonate group, a sulfamoyl group, a sulfonamide group, a sulfonyl group, a silyl group, or a trifluoromethyl group.

In certain embodiments, Y is absent, $R_3$ is a $C_1$-$C_{12}$ substituted or unsubstituted alkyl group, and $R_4$-$R_8$ are hydrogen.

In a particular embodiment, the chemosensing agent is defined by the structure shown below.

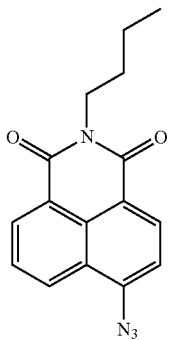

A. Fluorophores

Chemosensing agents for the detection and quantification of $H_2S$ contain a fluorophore. The fluorophore possesses photophysical properties which vary based on the identity and chemical properties of substituents on the fluorophore core. As a result, changes in the spectroscopic properties of the fluorophore accompany reaction of the attached reactive functional group with $H_2S$.

The fluorophore is selected to possess photophysical properties which facilitate the observation and/or analysis of the spectroscopic properties of the fluorophore. For example, in certain embodiments, the fluorophore possesses a fluorescence quantum yield that facilitates observation and measurement of the chemosensing agent's fluorescence. In some cases, the fluorophore possesses a quantum yield of at least 0.10, 0.15, 0.20, 0.25, 0.30, 0.35, 0.40, 0.45, 0.50, 0.55, 0.60, 0.65, 0.70, 0.75, 0.80, 0.85, or 0.90 in aqueous solution.

In some cases, the chemosensing agent is designed for sensing in biological samples. In biological samples, background fluorescence from cells, tissues and biological fluids (referred to as autofluorescence) can complicate analysis of the fluorescence of the chemosensing agent. In some cases, the fluorophore does not possess an emission maximum in a spectral region which substantially overlaps with the autofluorescence of biological samples. In certain embodiments, the fluorophore possesses an emission maximum greater than 430 nm, 440 nm, 450 nm, 460 nm, 470 nm, 480 nm, 490 nm, 500 nm, 510 nm, 520 nm, 530 nm, 540 nm, 550 nm, 560 nm, 570 nm, 580 nm, 590 nm, 600 nm, 610 nm, 620 nm, 630 nm, 640 nm, 650 nm, 660 nm, 670 nm, 680 nm, 690 nm, or 700 nm in aqueous solution. In certain embodiments, the fluorophore possesses an emission maximum in aqueous solution between 430 nm and 700 nm, more preferably between 450 nm and 700 nm, most preferably between 480 nm and 700 nm. In some embodiments, the fluorophore possesses an emission maximum in aqueous solution between 430 nm and 1200 nm, more preferably between 450 nm and 1200 nm, most preferably between 480 nm and 1200 nm.

In preferred embodiments, the fluorophore is selected to possess the photophysical properties, including fluorescence quantum yield and emission maxima, desired for a particular sensing application. In some embodiments, the fluorophore possesses a high quantum yield and emits at a long wavelength. In a particular embodiment, the fluorophore possesses an emission maximum greater than 450 nm and a quantum yield of greater than 0.10 in aqueous solution.

Any suitable fluorophore may be incorporated into the chemosensing agents described above. Fluorophores useful in chemosensing agents typically contain an extended conjugation path (e.g., alternating single and double bonds) over which pi electrons are delocalized. The fluorophore can be aromatic, meaning it contains one or more aromatic rings, or non-aromatic (e.g., a linear structure). In preferred embodiments, the fluorophore contains one or more aromatic rings.

In some embodiments, the fluorophore is an organic or organometallic small molecule. Suitable small molecule fluorophores are known in the art, and include, but are not limited to, xanthene and xanthene derivatives, such as fluorescein or a fluorescein derivative, rhodamine, Oregon green, eosin, Texas red, and Cal Fluor dyes; cyanine and cyanine derivatives, such as indocarbocyanine, oxacarbocyanine, thiacarbocyanine, merocyanine, and Quasar dyes; naphthalene derivatives, such as dansyl and prodan derivatives and naphthalimide and naphthalimide derivatives; coumarin and derivatives thereof; oxadiazole derivatives, such as pyridyloxazole, nitrobenzoxadiazole and benzoxadiazole; pyrene derivatives, such as cascade blue; oxazine derivatives, such as Nile red, Nile blue, cresyl violet, and oxazine 170; acridine derivatives; such as proflavin, acridine orange, and acridine yellow; arylmethine derivatives, such as auramine, crystal violet, and malachite green; tetrapyrrole derivatives, such as porphin, phtalocyanine, and bilirubin; fluorene derivatives; CF® dye (available from Biotium); BODIPY® (available from Invitrogen); Alexa Fluor® (available from Invitrogen); DyLight Fluor® (available from Thermo Scientific); Atto® and Tracy® available from Sigma Aldrich; and FluoProbes® (available from Interchim). Other suitable fluorophores include those described in Lakowicz, J. R. "Principles of Fluorescence Spectroscopy", $2^{nd}$ Ed., Plenum Press, New York, 1999.

Suitable fluorophores can also include macromolecules, such as conjugated polymers. In some embodiments, the fluorophore is a conjugated polymer, such as a poly(arylene ethynylene), containing one or more sidechains that contain reactive functional groups.

B. Reactive Functional Groups

Chemosensing agents for $H_2S$ contain one or more reactive functional groups. The one or more reactive functional groups can, independently for each occurrence, be any chemical moiety which reacts with $H_2S$ to form a different chemical moiety. In certain embodiments, the reactive functional group is a chemical moiety that is reduced upon contact with sulfide. Examples of suitable reactive functional groups include azido groups and substituted or unsubstituted anthraquinones.

In preferred embodiments, the one or more reactive functional groups are azido groups. Azido groups can be readily reduced by sulfide to form amines (F. Kazemi, A. R. Kiasat, S. Sayyahi, *Phosphorus, Sulfur, and Silicon* 2004, 179, 1813-1817).

C. Activating Groups

Chemosensing agents can optionally contain an activating group to which the reactive functional group is covalently attached. In certain embodiments, the activating group is a separate from the fluorophore. In other embodiments, a portion of the fluorophore can function as the activating group.

The activating group can be used to increase or decrease the rate of reaction of the reactive functional group with $H_2S$. By increasing or decreasing the rate of reaction of the reactive functional group with H₂S, chemosensing agents with the desired reaction rate for particular sensing applications can be prepared. The chemosensing agent need not contain an activating group if the rate of reaction of the reactive functional group with H₂S is appropriate for the intended sensing application(s).

In some embodiments, the rate of reaction, e.g., reduction, of the functional group may be too slow to be practical for the intended in vivo or in vitro applications. Therefore, the rate of reduction may be increased by introducing an activating group that increases the rate of reaction of the reactive functional group with H₂S. For example, the presence of an electron withdrawing group, particularly a strongly electron withdrawing group, can increase the rate of reduction of adjacent azido groups, for example by altering the redox potential of the reactive functional group.

In certain embodiments, the activating group is an electron withdrawing group that increases the rate of reaction of the attached reactive functional group with H₂S. In certain embodiments, the activating group increases the rate of reaction of a chemosensing agent containing a reactive functional group with H₂S by at least two-fold, more preferably by at least five-fold, most preferably by at least ten-fold as compared to the same chemosensing agent without an activating group.

In some embodiments, the chemosensing agent is designed to possess a short equilibration time upon exposure to H₂S. In some embodiments, the fluorescence intensity of the chemosensing agent, as measured at the maximum emission wavelength, reaches equilibrium less than ten minutes, nine minutes, eight minutes, seven minutes, six minutes, five minutes, four minutes, three minutes, two minutes, one minute, 45 seconds, or 30 seconds after contact with the H₂S. In certain embodiments, the fluorescence intensity of the chemosensing agent, as measured at the maximum emission wavelength, reaches equilibrium less than ten minutes after contact with the H₂S, more preferably less than six minutes after contact with the H₂S, most preferably less than three minutes after contact with the H₂S.

Suitable electron withdrawing groups include carbonyl groups, sulfoxide groups, and sulfonyl groups as well as carbon atoms containing one or more electron withdrawing substituents, such as a nitro group, cyano group, trifluoromethyl group, or combination thereof. In particular embodiments, the activating group is an electron withdrawing sulfonyl group or carbonyl group.

In other embodiments, the activating group may be an electron donating group that decreases the rate of reaction of the reactive functional group with H₂S.

D. Spacer Groups

Chemosensing agents can optionally contain a spacer group between the fluorophore and the activating group, if present, and the reactive functional group When present, the spacer group is selected so as to not significantly adversely affect the rate of reaction of the reactive functional group with sulfide and/or the ability of the reaction product to be spectroscopically detected or measured. In certain embodiments, the spacer group is conjugated to the fluorophore so as to provide a path of conjugation between the activating group, if present, and the reactive functional group Examples of suitable spacers include aryl groups, heteroaryl groups, alkenyl groups, and alkynyl groups.

E. Synthesis of Chemosensing Agents

Chemosensing agents can be prepared using synthetic methods known in the art. Representative methodologies for the preparation of chemosensing agents are discussed below. The appropriate route for synthesis of a given chemosensing agent can be selected in view of a number of factors, such as the structure of the chemosensing agent, the identity and connectivity of the fluorophore, reactive functional group, spacer, and activating group which make up the chemosensing agent, as well as the structure of the chemosensing agent as a whole as it relates to compatibility of functional groups, protecting group strategies, and the presence of labile bonds.

In addition to the synthetic methodologies discussed below, alternative reactions and strategies useful for the preparation of the chemosensing agents disclosed herein are known in the art. See, for example, March, "Advanced Organic Chemistry," 5th Edition, 2001, Wiley-Interscience Publication, New York).

Generally, chemosensing agents are prepared by functionalization of a fluorophore to incorporate one or more reactive functional groups, linking groups, and/or activating groups. A wide variety of fluorophores are commercially available in the art. Chemosensing agents can be prepared via covalent modification of a commercially available fluorophore to incorporate a reactive functional group (and optionally a linking group and/or an activating group). Alternatively, the fluorophore may be synthesized using methods known in the art, and then covalently modified to incorporate a reactive functional group (and optionally a linking group and/or an activating group). Methods of preparing suitable fluorophores, including those described above, are well known in the art. See, for example, R. P. Haugland, "Covalent Fluorescent Probes", In Excited States of Biopolymers, R. F. Steiner, Ed., Plenum Press: New York, 1983.

An exemplary synthesis of a chemosensing agent containing an azide reactive functional group and a sulfonyl activating group (dansyl azide, DNS-Az, 2) is shown in scheme 1.

Scheme 1:

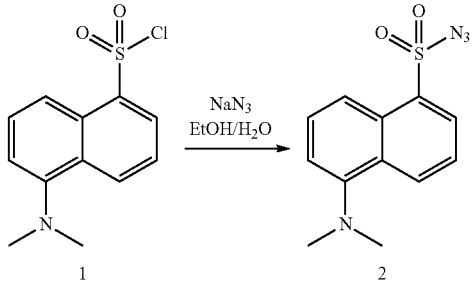

Commercially available fluorophores containing one or more sulfonyl chloride substituents offer a convenient starting point for the synthesis of chemosensing agents containing an azide reactive functional group and a sulfonyl activating group. For example, chemosensing agent 2 can be readily prepared from commercially available dansyl chloride (1) by treatment of 1 with sodium azide in an ethanol/water mixture.

A variety of fluorophores containing sulfonyl chloride groups are commercially available from suppliers including Oakwood Products, Inc (West Columbia, S.C.) Sigma Aldrich (St. Louis, Mo.). These commercially available fluorophores can be used to prepare chemosensing agents containing an azide reactive functional group and a sulfonyl activating group. Fluorophores containing sulfonyl chloride groups can also be prepared using standard synthetic techniques. For example, fluorophores containing a sulfonic acid group can be readily converted to the corresponding sulfonyl chloride by treatment with thionyl chloride.

An exemplary synthesis of a chemosensing agent containing a naphthalimide fluorophore linked to an azide reactive functional group (6) is shown in scheme 2. Reaction of commercially available 4-bromo-1,8-naphthalic anhydride (4) with n-butylamine affords 5. Subsequent reaction of with sodium azide in an water/dimethylformamide mixture affords 6. 6 is relatively non-fluorescent; however, upon exposure to 100 µM $H_2S$ in 1:1 phosphate buffer/acetonitrile, an approximately 100-fold increase in fluorescence intensity is observed.

Scheme 2:

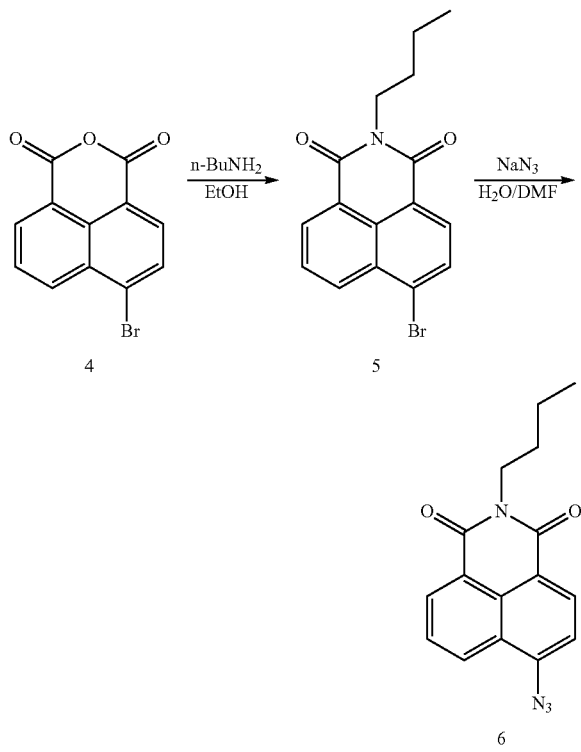

Chemosensing agents containing alternative reactive functional groups, fluorophores, linking groups, and activating groups can be prepared using similar methods known in the art.

III. Methods of Use

Chemosensing agents can be used to detect and/or quantify $H_2S$. $H_2S$ can be detected or quantified by observing and/or measuring a spectroscopically observable change in the chemosensing agent induced by the presence of $H_2S$. This change can be a change in the absorbance of the chemosensing agent (i.e., color), a change in the fluorescence of the chemosensing agent, or a combination thereof.

In some cases one or more spectroscopically observable changes in a chemosensing agent is qualitatively observed to detect the presence of $H_2S$ in a sample. For example, the absorbance of the chemosensing agent (i.e., color) of the fluorescence of the chemosensing agent (under irradiation by, for example a UV blacklight) can be observed by the naked eye to qualitatively assess the presence of $H_2S$ in a sample. In other embodiments, one or more spectroscopically observable changes in a chemosensing agent are measured as part of an assay to quantify the amount of $H_2S$ in a sample.

In certain embodiments, the chemosensing agents are used in fluorescence assays for the detection and/or quantification of sulfide. In general, fluorescence assays using the chemosensing agents described above involve contacting a sample with a chemosensing agent and measuring or observing the fluorescence of the chemosensing agent. As described above, $H_2S$ reacts with the chemosensing agent to alter the fluorescence of the chemosensing agent in one or more ways. Essentially any change in the photophysical properties of the chemosensing agent may be used to determine the presence of $H_2S$ and, optionally, the concentration of $H_2S$ in a sample.

Chemosensing agents can be used for solution-based assays for the detection and quantification of $H_2S$. In some embodiments, the chemosensing agents are used to detect or measure $H_2S$ in an aqueous solution.

Chemosensing agents can be immobilized on a solid support, either via covalent or non-covalent interactions, and used to detect $H_2S$ in a gas or liquid stream passed over the immobilized chemosensing agent. Suitable solid supports include, but are not limited to, polymer beads, polymer films, silica gel, and woven and non-woven fabrics.

In preferred embodiments, the fluorescence assay possesses a detection limit of less than 100 µM, more preferably less than 50 µM, more preferably less than 25 µM, most preferably less than 10 µM.

Chemosensing agents can be used to detect or quantify $H_2S$ in water samples taken from wells, municipal water sources, and natural water sources, for example to ensure water quality and safety. Chemosensing agents can be used to detect and/or quantify $H_2S$ in liquid effluents and gas emissions industrial settings, including paper and pulp mills, asphalt plants, and sewage treatment facilities. Chemosensing agents can also be used to detect and/or quantify $H_2S$ in gaseous fuel streams. Examples of gaseous fuel streams include biogas, frac gas, gasified biomass, gasified coal/bitumen, gases from natural gas and oil wells, gases from tar sands, landfill gases, syngas, flare gas, and gases from agricultural and livestock operations.

In other embodiments, the chemosensing agents are used in a fluorescence assay to detect and/or quantify $H_2S$ concentrations in a biological sample. In certain embodiments, chemosensing agents are employed in an in vitro bioassay for the detection or quantification of $H_2S$ is a biological sample, such as blood or blood plasma.

A. Instrumentation

The fluorescence of the chemosensing agents may be detected by any suitable fluorescence analyzer. Fluorescence analyzers typically contain a light source for excitation of the fluorophore and a sensor for detecting emitted light. In addition, fluorescence analyzers can optionally contain one or more diffraction gratings, dichroic mirrors, and/or filters that are used to control the wavelength of the excitation light and/or control the wavelength of light detected by the sensor. In some embodiments, the device is coupled to a signal amplifier and a computer for data processing. Examples of suitable fluorescence analyzers include commercially available fluorometers, spectrofluorometers, flow cytometers, and fluorescence microscopes.

Alternatively, for some qualitative assays, a fluorescence analyzer may not be required. For example, in some assays, the presence of an analyte may be determined by visually observing fluorescence by the naked eye.

B. General Aspects of Fluorescence Assays

Fluorescence assays involve the observation and/or measurement of changes in one or more of the fluorescence of a chemosensing agent. The change may take one or more of several forms, including a change in emission spectra, a change in the intensity of the fluorescence (i.e., fluorescence quantum yield), and a change in the fluorescence lifetime. These changes may be either in the positive or negative direction and may be of a range of magnitudes, which preferably will be detectable as described below.

The emission spectra of a chemosensing agent can be measured using a spectrofluorometer. The spectrofluorometer uses a high intensity light source with a particular wavelength (or interval of wavelengths) to excite the chemosensing agent. The spectrofluorometer then measures the intensity of light emitted by the chemosensing agent at a range of different wavelengths, called an emission spectra. Changes in the maximum emission wavelength or the shape of the emission spectra that are caused by $H_2S$ in a sample may be used to determine the presence or concentration of $H_2S$ in the sample.

In embodiments where $H_2S$ is detected or quantified by measuring the change in the maximum emission wavelength of the chemosensing agent, the chemosensing agent will preferably be designed to exhibit a large change in maximum emission wavelength upon exposure to $H_2S$. In some embodiments, the maximum emission wavelength of the chemosensing agent shifts by more than 50 nm, more preferably by more than 75 nm, most preferably by more than 100 nm upon exposure to $H_2S$.

Changes in the maximum emission wavelength can also be observed with the naked eye, for example with the use of a handheld blacklight, to qualitatively determine the presence of $H_2S$ in a sample.

The fluorescence quantum yield of a chemosensing agent can be measured using methods known in the art. See, for example, Lakowicz, J. R. "Principles of Fluorescence Spectroscopy", $2^{nd}$ Ed., Plenum Press, New York, 1999. Generally, the fluorescence quantum yield of the agent is obtained by comparison of the integrated area of the corrected emission spectrum of the chemosensing agent with that of a reference solution.

A change in the fluorescence quantum yield of the chemosensing agent upon exposure to $H_2S$ may be used as the basis for detecting the presence of $H_2S$ in a sample, and may optionally be used to determine the concentration $H_2S$ in a sample.

In some embodiments, the chemosensing agent will preferably be designed to exhibit a large change in fluorescence quantum yield upon exposure to $H_2S$. In some embodiments, exposure of the chemosensing agent to $H_2S$ results in at least a 10% reduction in the fluorescence quantum yield of the chemosensing agent, more preferably at least a 25% reduction in the fluorescence quantum yield of the chemosensing agent, more preferably at least a 50% reduction in the fluorescence quantum yield of the chemosensing agent, more preferably at least a 75% reduction in the fluorescence quantum yield of the chemosensing agent, most preferably at least a 90% reduction in the fluorescence quantum yield of the chemosensing agent. In other embodiments, exposure of the chemosensing agent to $H_2S$ results in at least a 25% increase in the fluorescence quantum yield of the chemosensing agent, more preferably at least a 50% increase in the fluorescence quantum yield of the chemosensing agent, more preferably at least a 75% increase in the fluorescence quantum yield of the chemosensing agent, more preferably at least a 100% increase in the fluorescence quantum yield of the chemosensing agent, more preferably at least a 500% increase in the fluorescence quantum yield of the chemosensing agent, most preferably at least a 1000% increase in the fluorescence quantum yield of the chemosensing agent.

The fluorescence lifetime of a chemosensing agent can also be measured using methods known in the art. Changes in the fluorescence lifetime upon exposure to $H_2S$ can also be used to determine the presence or concentration of $H_2S$ in the sample.

C. In Vitro and In Vivo Fluorescence Assays

In one variation, $H_2S$ in a biological sample is detected and/or quantified by contacting the sample with a chemosensing agent. The fluorescence of the solution is then measured using one of the above-described devices, preferably a spectrofluorometer. Optionally, the fluorescence of the solution may be compared against a set of standard solutions containing known quantities of $H_2S$, i.e., the analyte. Comparison to standards may be used to calculate the concentration of the analyte, i.e., the ligand.

In biological samples, the concentration of $H_2S$ may change over time. The chemosensing agent may also be used as a probe to monitor changing levels of $H_2S$ in a biological sample over time.

The chemosensing agent may be used to detect or quantify $H_2S$ in vitro. In certain embodiments, the in vitro sample is a biological fluid, lysate, homogenate, or extract. The sample may also be an environmental sample such as a water sample, soil sample, soil leachate or sediment sample.

In certain embodiments, cells (e.g., bacterial or eukaryotic cells) or tissue are contacted with a chemosensing agent, and the presence or amount of $H_2S$ in the cells or tissue is determined using a fluorescence microscope. In order to observe co-localization of $H_2S$ and other analytes, the cells or tissue may also be simultaneously contacted with sensors for other analytes. The chemosensing agent may be used to detect and/or quantify intercellular and intracellular $H_2S$.

EXAMPLES

Example 1

Dansyl Azide (DNS-Az) as a Selective and Efficient Fluorescent Chemosensor for $H_2S$ in Aqueous Solution Dansyl is a common fluorophore, and is well known for its strong fluorescence and long emission wavelength. A chemosensing agent for the detection and quantification of $H_2S$ was designed using by incorporating a reactive functional group into the dansyl fluorophore. For purposes of initial investigation, an azido group was incorporated into the dansyl fluorophore to take advantage of the known reduction of azidos group by $H_2S$ (F. Kazemi, A. R. Kiasat, S. Sayyahi, *Phosphorus, Sulfur, and Silicon* 2004, 179, 1813-1817).

Generally, the rate of reduction of azides by sulfides is too slow to provide for 'real-time' or rapid detection and quantification of $H_2S$, particularly in biological samples. However, by connecting the azide to an activating group (e.g., an electron withdrawing sulfonyl group), the reduction of the azido group to an amino group proceeds at an accelerated rate. Because of the difference in electronegativity of azido- and amino-groups and the added degree of rotational freedom for the azido group, reduction of the sulfonyl azide to the sulfonamide triggers a change in the electronic properties of the attached dansyl fluorophore. The synthesis and fluorescence response of the dansyl azide chemosensing agent are illustrated in scheme 3 (below).

Scheme 3:

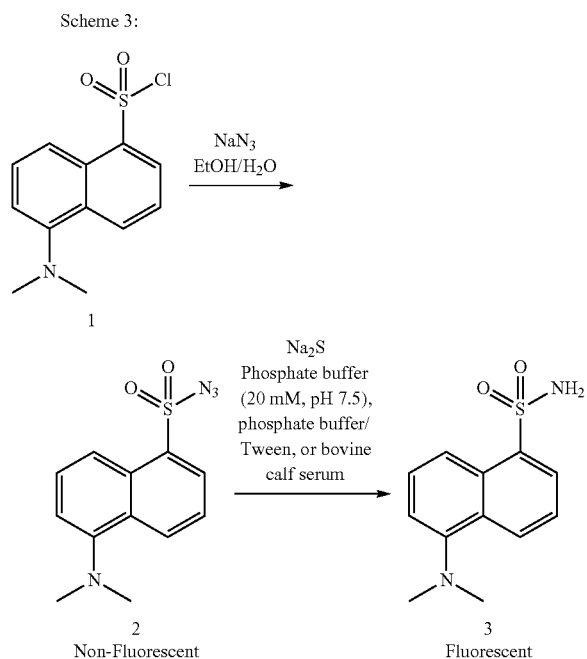

Materials and Methods

All reagents were purchased from Aldrich. $^1$H NMR and $^{13}$C NMR spectra were recorded at 400 and 100 MHz, respectively, on a Bruker Avance 400 MHz NMR spectrometer. Mass spectral analyses were performed by the Mass Spectrometry Facilities at Georgia State University. HPLC was performed on a Hewlett Packard Series 1100 HPLC (column: Agilent Prep-C18 5 μM, 4.6×250 mm). UV-Vis absorption spectra were recorded on a Shimadzu PharmaSpec UV-1700 UV-Visible spectrophotometer. Fluorescence spectra were recorded on a Shimadzu RF-5301PC fluorometer.

Synthesis and Characterization of Dansyl Azide (DNS-Az):

A suspension of dansyl chloride (1,250 mg, 0.93 mmol) in 15 mL of ethanol (EtOH) was added dropwise into a stirred solution of sodium azide in 7 mL of a mixed solvent ($H_2O$/EtOH, 1:1). Then the reaction mixture was stirred at room temperature for 3 hr. The organic solvent was evaporated in vacuum, and the aqueous solution was extracted by DCM. The combined organic layers was washed with brine and then dried over $MgSO_4$. Solvent evaporation gave the crude product, which was purified by flash chromatography to give dansyl azide (2, 107 mg, 42%) as a light yellow oil. $^1$H NMR (DMSO-$d_6$): 8.68-8.66 (d, J=8.4 Hz, 1H), 8.40-8.38 (m, 1H), 8.07-8.05 (d, J=8.0 Hz, 1H), 7.77-7.73 (m, 2H), 7.75 (s, 2H), 7.36-7.34, (d, J=7.8 Hz), 2.86 (s, 6H), $^{13}$C NMR (CDCl$_3$): 152.2, 133.7, 132.7, 130.1, 130.1, 129.7, 129.3, 123.0, 118.8, 115.9, 45.4, ESI-MS: m/z 277.1 (M+1)$^+$.

Synthesis and Characterization of Dansyl Amide (DNS-NH$_2$):

A solution of sodium sulfide (43 mg, 0.18 mmol) in 0.4 mL $H_2O$ was added into a stirred solution of 2 in 17 mL acetonitrile. The reaction mixture was stirred for 2 hr at room temperature. Then solvents were evaporated under vacuum. The residue was purified by flash chromatography (DCM/MeOH 50:1) to give pure DNS-NH$_2$ (40 mg, 91%) as a yellow solid. $^1$H NMR (DMSO-$d_6$): 8.44-8.42 (d, J=8.4 Hz, 1H), 8.30-8.28 (d, J=8.8 Hz, 1H), 8.13-8.11 (m, 1H), 7.63-7.56 (m, 2H), 7.59 (s, 2H), 7.27-7.25, (d, J=8.4 Hz), 2.83 (s, 6H), $^{13}$C NMR (DMSO-$d_6$): 151.8, 140.2, 129.5, 129.4, 129.2, 128.0, 126.8, 124.0, 120.0, 115.5, 45.5, ESI-MS: m/z 251.1 (M+1)$^+$.

Detection of H$_2$S in Aqueous Solution:

DNS-Az was dissolved in acetonitrile or ethanol to make a stock solution of 30.0 mM. Then 10 μL of the stock solution was added into 1.0 mL of sample solution containing 0-100 μM of H$_2$S. The sample was mixed well for 1-5 minutes (depending on the reaction medium) and measured using a fluorometer ($\lambda_{Ex}$=340 nm). The reading was then compared to the standard curve to obtain the concentration of H$_2$S.

Detection of H2S in Mouse Blood:

DNS-Az was dissolved in acetonitrile or ethanol to prepare a 50.0 mM stock solution. Blood was drawn from the inferior vena cava of male C57BL6/J mice. Blood (100 μL×4) was added into Eppendorf® tubes with DNS-Az (0.4 μL, final concentration 200 μM). Na$_2$S was spiked into each sample to a final concentration of 10, 50 and 100 μM. The samples were mixed thoroughly, and centrifuged. Then, 50 μL of serum was transferred from each sample into a 96-well plate. Zero point was obtained by trapping sulfide with ZnCl$_2$ (1 μL in 100 μL blood, final concentration 1 mM) followed by centrifugation and addition of DNS-Az into serum. The plate was read on a micro-plate reader (excitation lamp filter 360 nm, emission filter 528 nm).

Results

DNS-Az (2) by itself is non-fluorescent. However, upon addition of H$_2$S, DNS-Az solution showed a strong fluorescence enhancement. The magnitude of the fluorescent enhancement was solvent-dependent. For example, when the experiments were conducted in 20 mM phosphate buffer (pH 7.5)/ACN 1:1, 150 fold of fluorescent intensity enhancement was observed with the addition 25 μM of sulfide. For a thorough understanding of the solvent effect, the following solvent systems were tested: acetonitrile, deionized water, 20 mM sodium phosphate buffer (pH 7.5), acetonitrile/water (1:1), acetonitrile/phosphate buffer (1:1), and 20 mM sodium phosphate buffer (pH 7.5) with 0.5% Tween-20 (FIG. 1). The strongest response was observed in acetonitrile with a maximum of 130-fold fluorescent intensity increase with the addition of 10 μM of H$_2$S. The solvent system that gave the smallest fluorescent intensity increases (about 8 fold) was phosphate buffer or water alone. The presence of sodium phosphate buffer did not affect the fluorescence intensity (FIG. 1). Very interestingly, addition of 0.5% of Tween-20, a commonly used additive in biological experiments as a buffer component, led to a substantial increase in the magnitude of the fluorescent intensity change of DNS-Az upon sulfide addition. In such a mixed solvent, addition of 25 μM of sulfide led to a 40-fold fluorescence enhancement. The detection limit was as low as 1 μM with an S/N of 3:1. HPLC, MS and NMR analysis confirmed that the fluorescence increase was due to the formation of dansyl-amide (3).

Figure 2:
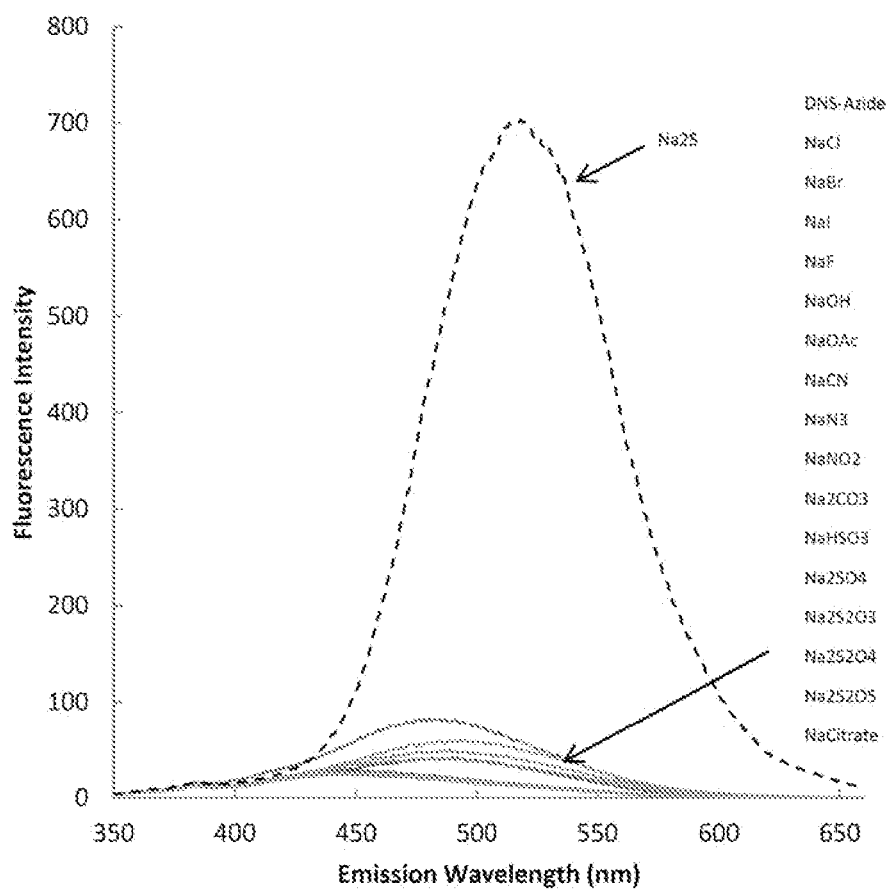
FIG. 2 is a graph showing fluorescence intensity (in arbitrary units) as a function of emission wavelength (nm) of DNS-Az (2, 100 μM in 20 mM sodium phosphate buffer with 0.5% Tween-20, $\lambda_{Ex}$=340 nm) by itself and upon addition of various anions (Na$_2$S (25 μM), NaCl (1 mM), NaBr (1 mM), NaI (1 mM), NaF (1 mM), NaOH (1 mM), NaOAc (1 mM), NaCN (1 mM), NaN$_3$ (1 mM), NaNO$_2$ (1 mM), Na$_2$CO$_3$ (1 mM), NaHSO$_3$ (100 μM), Na$_2$SO$_4$ (1 mM), Na$_2$S$_2$O$_3$ (1 mM), Na$_2$S$_2$O$_4$ (100 μM), Na$_2$S$_2$O$_5$ (100 μM), Na$_2$HPO$_3$ (1 mM), and sodium citrate (1 mM)). The fluorescence spectra obtained upon addition of Na$_2$S (25 μM) to DNS-Az is shown in a dashed line. All other fluorescence spectra are shown in solid gray lines.
Figure 10:
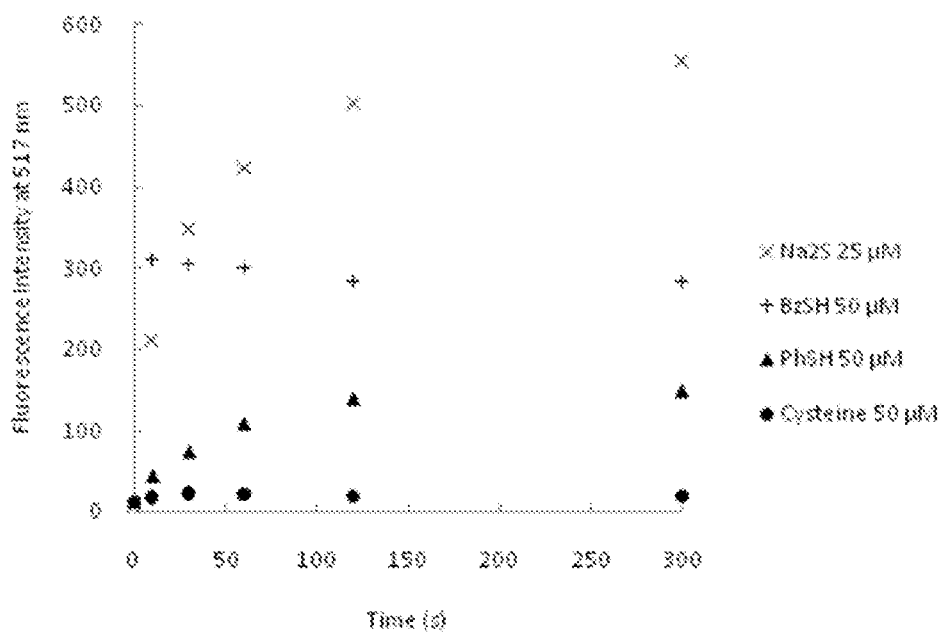
FIG. 10 is a graph showing fluorescence intensity at 517 nm (in arbitrary units) of DNS-Az (2) (100 μM) as a function of time with Na$_2$S (x, 25 μM), benzyl mercaptan (+, BzSH, 50 μM), thiophenol (▲, PhSH, 50 μM), and cysteine (●, 50 μM) in 20 mM phosphate buffer/0.5% Tween-20.
Figure 11:
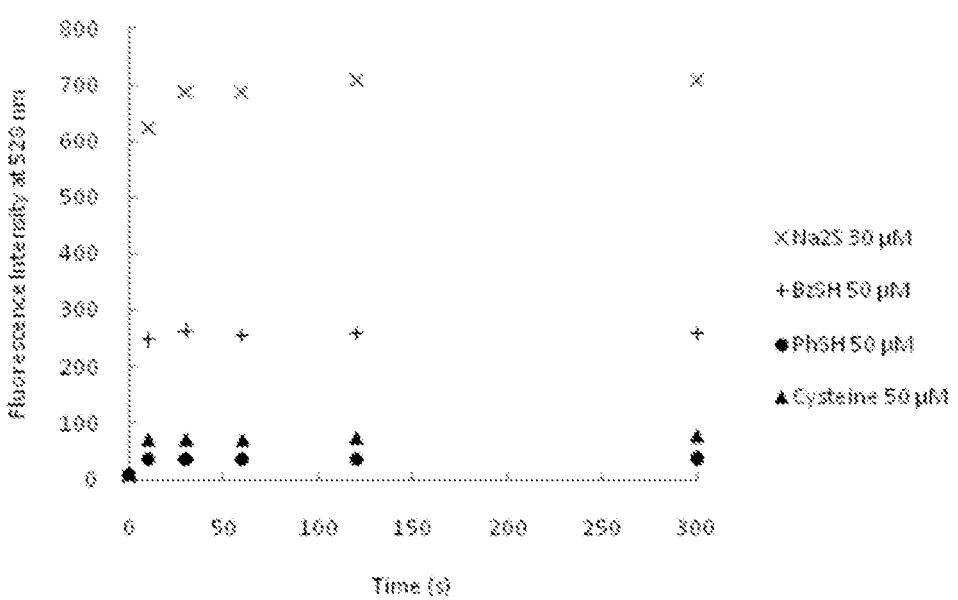
FIG. 11 is a graph showing fluorescence intensity at 528 nm (in arbitrary units) of DNS-Az (2) (100 μM) as a function of time with Na$_2$S (x, 30 μM), benzyl mercaptan (+, BzSH, 50 μM), thiophenol (▲, PhSH, 50 μM), and cysteine (●, 50 μM) in 20 mM phosphate buffer/acetonitrile 1:1.
Figure 12:
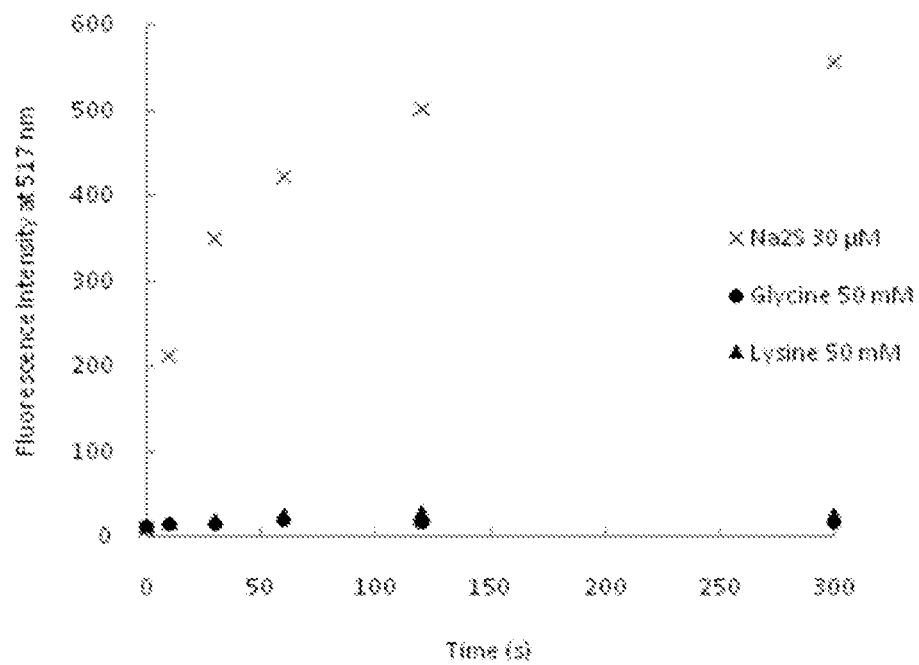
FIG. 12 is a graph showing fluorescence intensity at 517 nm (in arbitrary units) of DNS-Az (2) (100 μM) as a function of time with Na$_2$S (x, 30 μM), lysine (▲, 50 mM) and glycine (●, 50 mM) in 20 mM phosphate buffer/0.5% Tween-20.

In order to study the selectivity of this chemosensing agent for sulfide, the fluorescent properties of DNS-Az (2) in the presence of various anions were examined in buffer/Tween. No comparable response was observed from other anions (FIG. 2). Since the detection is based on the reducing property of sulfide, other possible reducing anions, such as iodide, bromide, fluoride, bisulfite, and thiosulfate, were also tested. Totally 18 anions were screened, no obvious response was observed for most of the anions at 1 mM, a concentration that is 40 fold higher than sulfide. Among all the anions, only NaHSO$_3$, Na$_2$S$_2$O$_4$, and Na$_2$S$_2$O$_5$ led to some fluorescent intensity increases. However, the extent of the fluorescence increase was far smaller than those caused by sulfide even when the concentrations of those anions were 4-fold higher than that of sulfide (FIG. 2). The response of DNS-Az (2) to other reducing agents, such as thiophenol, benzyl mercaptan and cysteine was also tested. Benzyl mercaptan was the only reducing agent that showed a strong enough fluorescence responses (about ⅕ of the response observed for sulfide, FIGS. 10 and 11) to potentially interfere with sulfide detection and quantification. However, this interference does not represent a practical problem for the detection of H$_2$S in biological systems because benzyl mercaptan is rarely present. DNS-Az was also found to be recalcitrant to the possible displacement reaction resulting from attack by an amino group. It showed very limited response to glycine and lysine at concentrations as high as 50 mM (FIG. 12).

Figure 3:
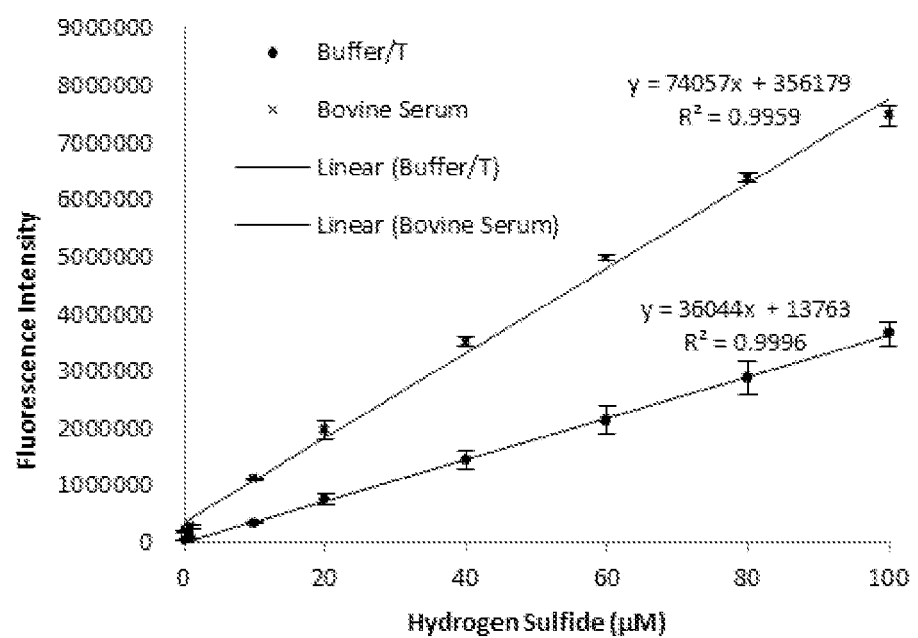
FIG. 3 is a graph showing fluorescence intensity (in arbitrary units) as a function of Na$_2$S concentration (μM) of DNS-Az (200 μM, Na$_2$S 0-100 μM) in commercial bovine calf serum (x) ($\lambda_{Ex}$=340 nm, $\lambda_{Em}$=535 nm) and of DNS-Az (100 μM, Na$_2$S 0-100 μM) in buffer/Tween (●) ($\lambda_{Ex}$=340 nm, $\lambda_{Em}$=535 nm). Data was collected in triplicate using a 96-well plate and a micro-plate reader. Best fit lines were plotted using the fluorescence data obtained in commercial bovine calf serum (y=74057x+356179; $R^2$=0.9959) and in buffer/Tween (y=36044x+13763; $R^2$=0.9996).

A linear relationship is always important for easy and accurate analysis. Thus, sulfide concentration-dependent study was performed. DNS-Az (2) reacts with sulfide essentially quantitatively even in aqueous solution. The fluorescence intensity at 517 nm showed a linear relationship in buffer/Tween against sulfide (FIG. 3). When sulfide concentration is higher than that of DNS-Az (2), the plot was found to reach a plateau (see FIG. 7B), which means that the stoichiometry of this reaction was 1:1.

Figure 4A:
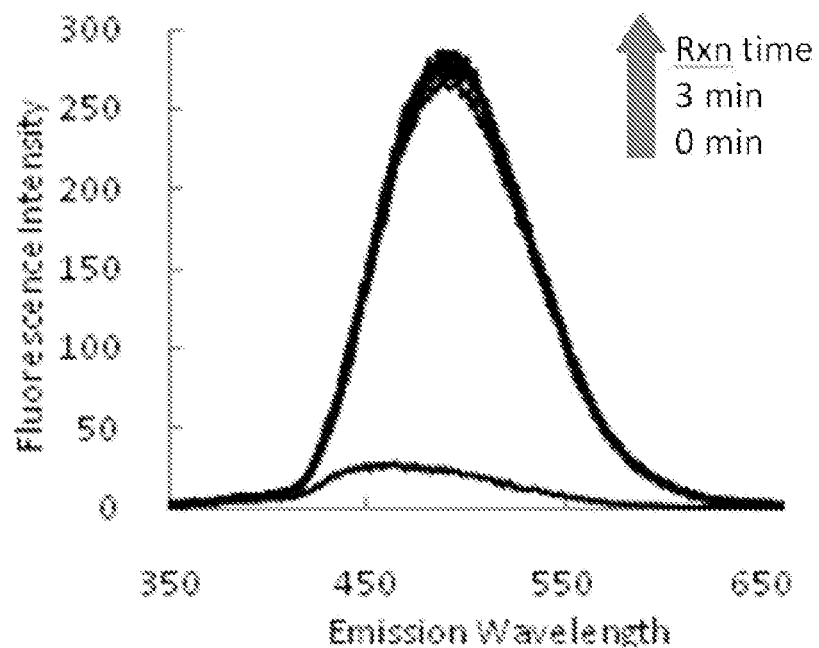
FIG. 4A is a graph showing fluorescence intensity (in arbitrary units) as a function of emission wavelength (nm) of DNS-Az (2, 100 μM) in bovine calf serum upon addition of sulfide (30 μM Na$_2$S). Emission spectra were collected prior to the addition of Na$_2$S, and over a period of 3 minutes following the addition of Na$_2$S. The emission spectra collected at varying intervals following the addition of Na$_2$S were overlayed, demonstrating an increase in fluorescence intensity over time following the addition of Na$_2$S.
Figure 4B:
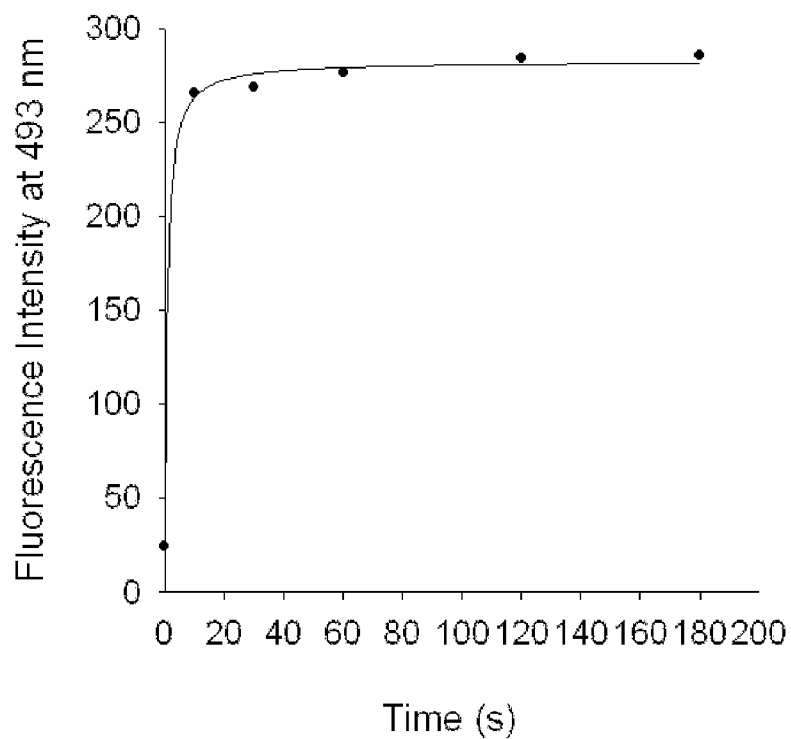
FIG. 4B is a graph showing fluorescence intensity (in arbitrary units) of DNS-Az (2, 100 μM) at 493 nm as a function of reaction time (seconds).
Figure 5:
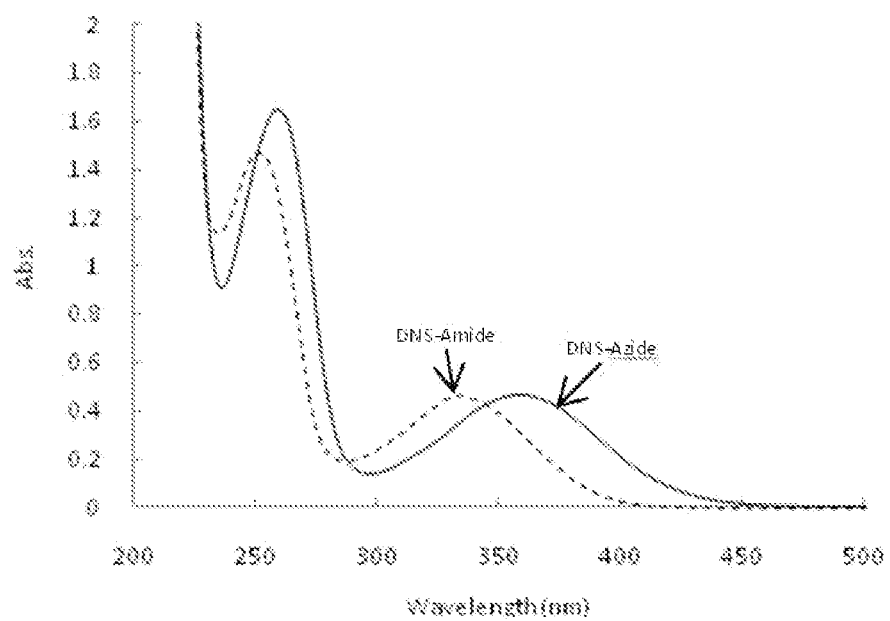
FIG. 5 is a graph showing UV absorption spectra (plotting absorbance as a function of wavelength (nm)) of DNS-Az (2, solid line) and DNS-NH$_2$ (3, dotted line), both in acetonitrile at 100 μM.
Figure 6A:
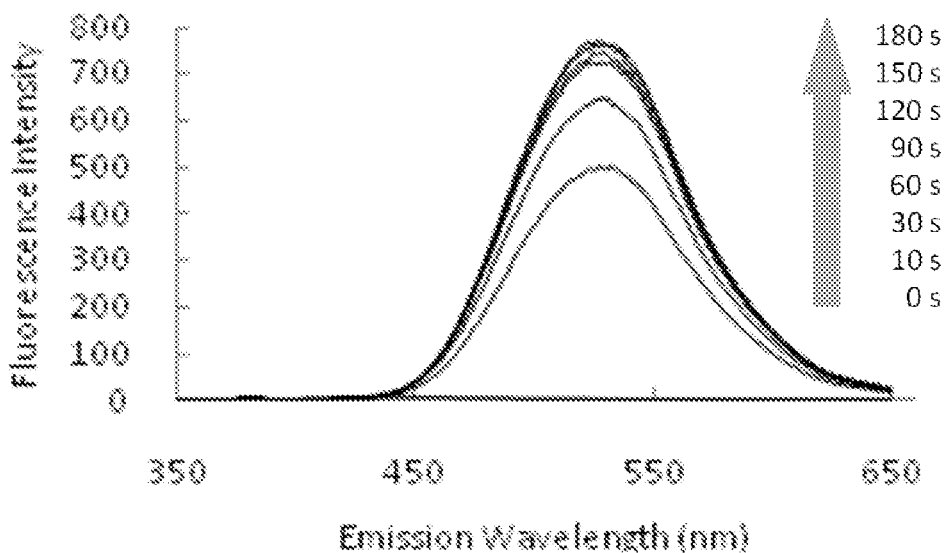
FIG. 6A is a graph showing fluorescence intensity (in arbitrary units) as a function of emission wavelength (nm) of DNS-Az (2, 100 μM) in 20 mM phosphate buffer:acetonitrile (1:1) upon addition of sulfide (30 μM Na$_2$S). Emission spectra were collected prior to the addition of Na$_2$S, and 10, 30, 60, 90, 120, 150, and 180 seconds after the addition of Na$_2$S. The emission spectra collected at varying intervals following the addition of Na$_2$S to DNS-Az were overlayed, demonstrating an increase in fluorescence intensity over time following the addition of Na$_2$S.
Figure 6B:
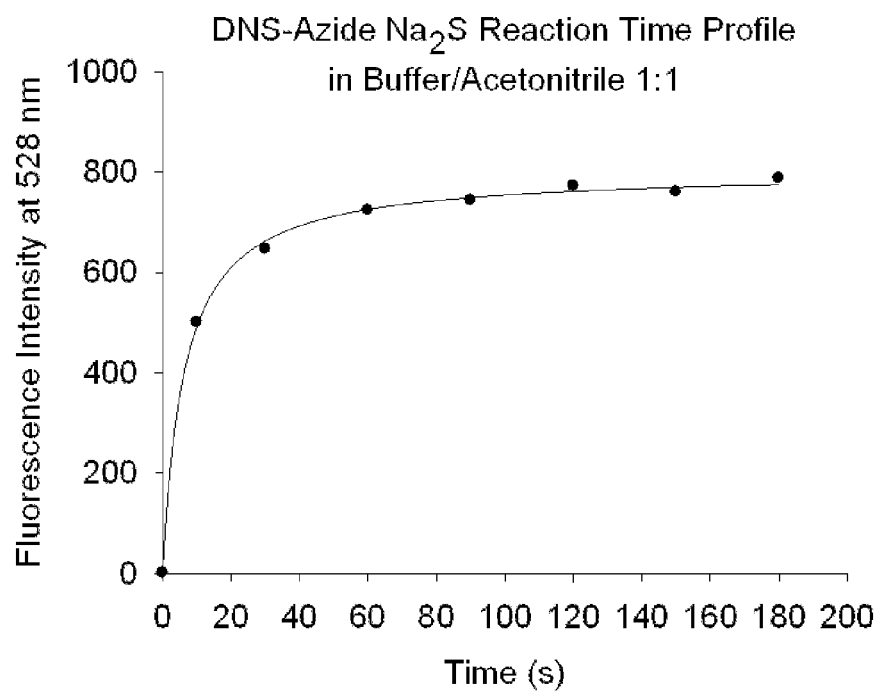
FIG. 6B is a graph showing fluorescence intensity (in arbitrary units) of DNS-Az (2, 100 μM) at 528 nm as a function of reaction time (seconds).
Figure 7A:
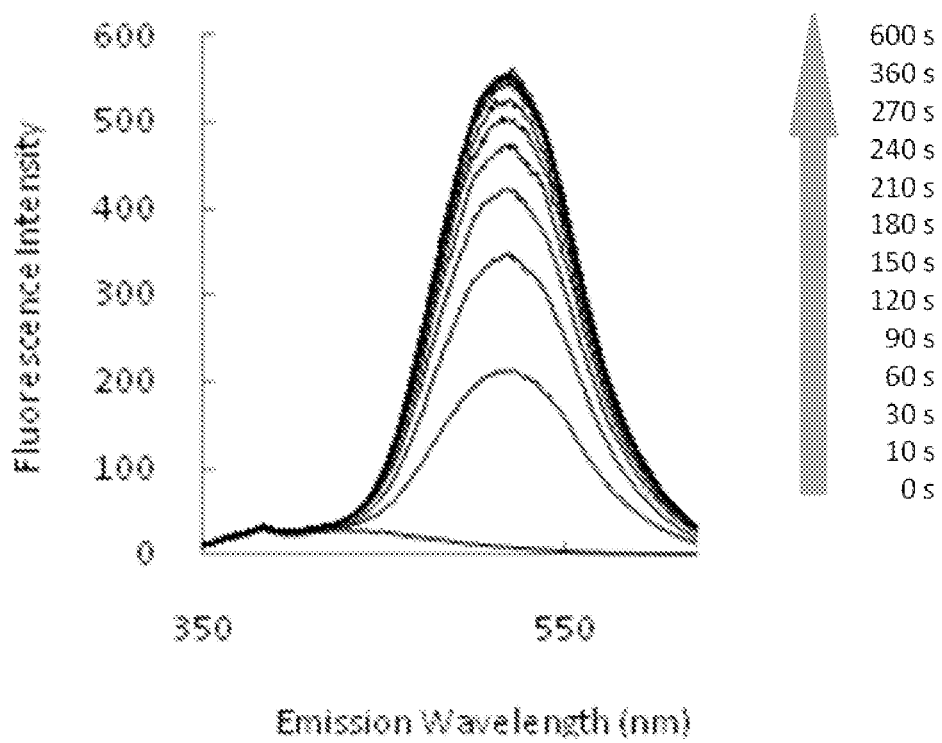
FIG. 7A is a graph showing fluorescence intensity (in arbitrary units) as a function of emission wavelength (nm) of DNS-Az (2, 100 μM) in 20 mM phosphate buffer/0.05% Tween-20 upon addition of sulfide (30 μM Na$_2$S). Emission spectra were collected prior to the addition of Na$_2$S, and 10, 30, 60, 90, 120, 150, 180, 210, 240, 270, 360, and 600 seconds after the addition of Na$_2$S. The emission spectra collected at varying intervals following the addition of Na$_2$S to DNS-Az were overlayed, demonstrating an increase in fluorescence intensity over time following the addition of Na$_2$S.
Figure 7B:
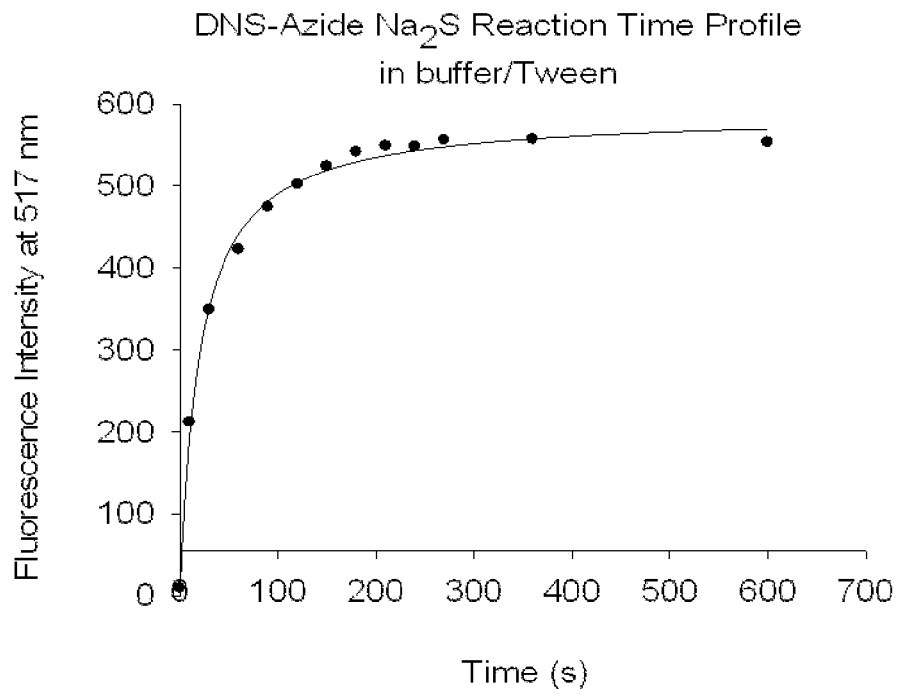
FIG. 7B is a graph showing fluorescence intensity (in arbitrary units) of DNS-Az (2, 100 μM) at 517 nm as a function of reaction time (seconds).
Figure 8:
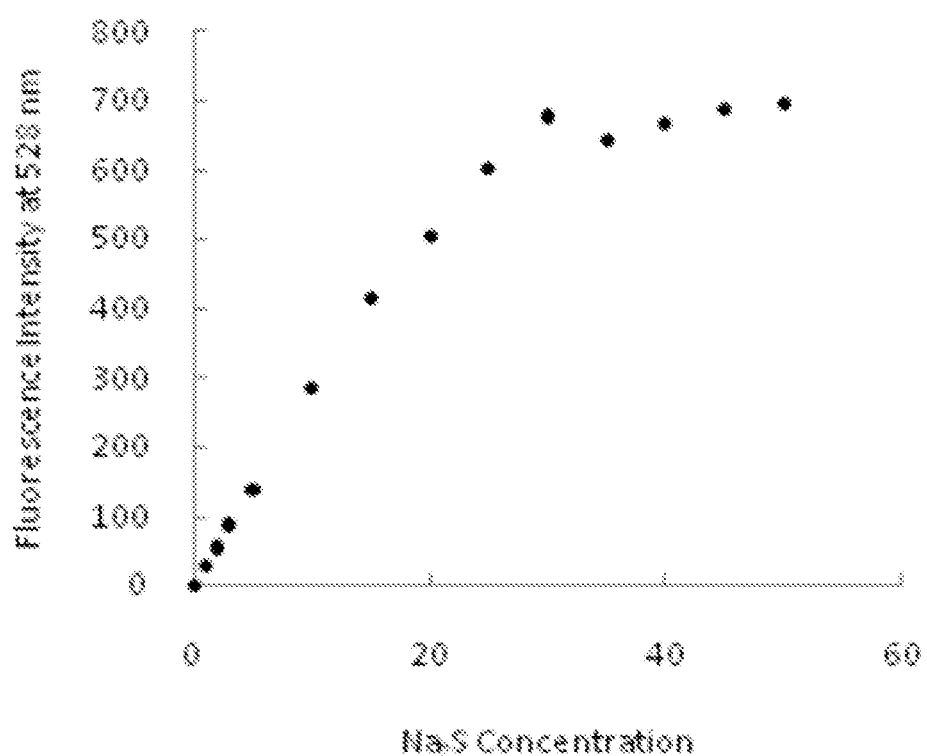
FIG. 8 is a plot of the fluorescence intensity (in arbitrary units) of 30 μM DNS-Az (2) in phosphate buffer:acetonitrile (1:1) at 528 nm upon the addition of varying amounts of Na$_2$S (0-50 μM).
Figure 9A:
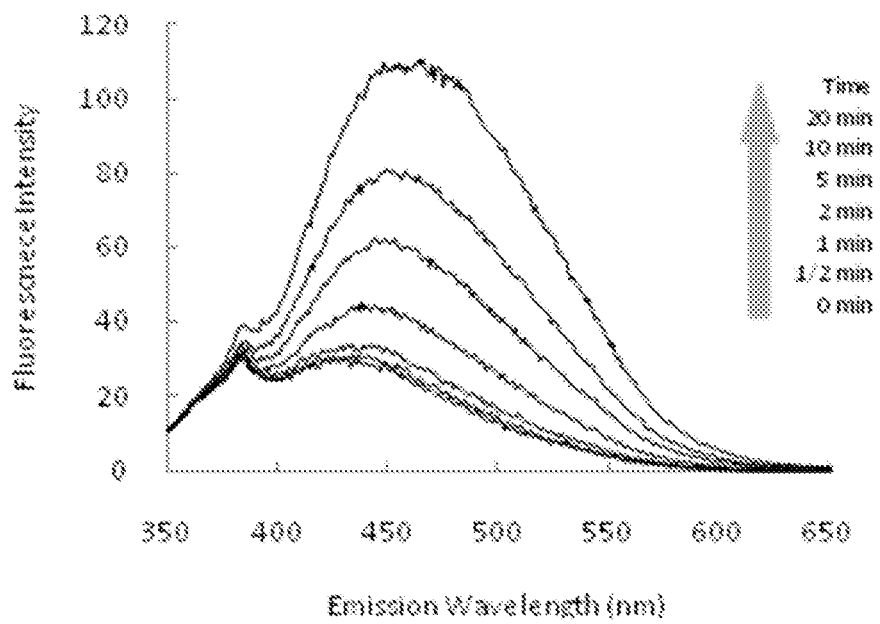
FIG. 9A is a graph showing fluorescence intensity (in arbitrary units) as a function of emission wavelength (nm) of DNS-Az (2) (25 μM) in 20 mM phosphate buffer/0.5% Tween. Emission spectra were collected prior to UV irradiation and after UV irradiation at 340 nm for 30 seconds, 1 minute, 2 minutes, 5 minutes, 10 minutes, and 20 minutes.
Figure 9B:
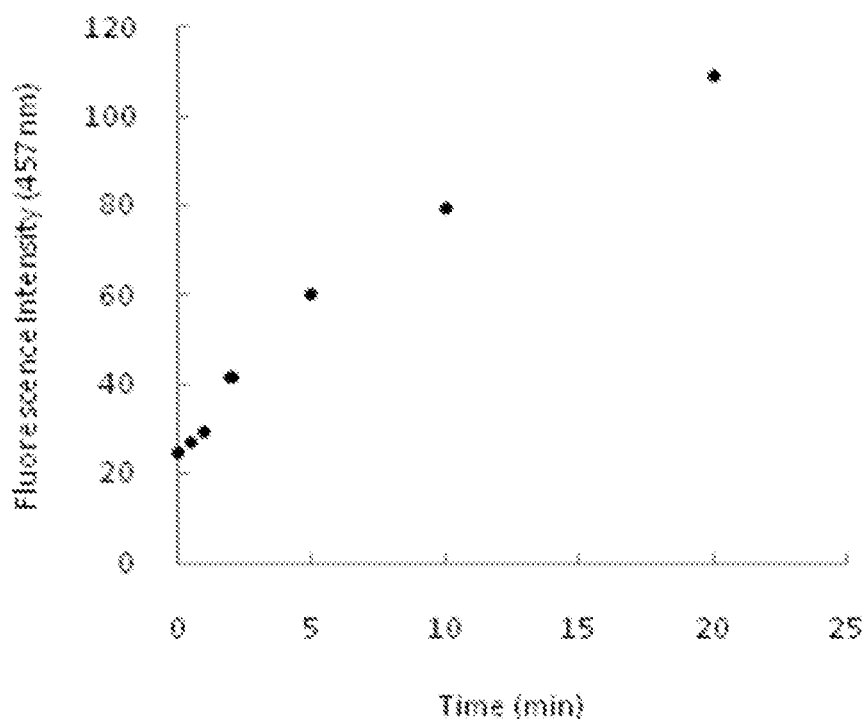
FIG. 9B is a dot plot showing fluorescence intensity (in arbitrary units) of DNS-Az (2) (25 μM in 20 mM phosphate buffer/0.5% Tween) at 457 nm as a function of UV irradiation time at 340 nm (in minutes).

Thus far, all the selectivity and linearity studies indicate that DNS-Az (2) can be used for the determination of sulfide concentrations in a biological sample. As a final test, DNS-Az (2) was evaluated in commercially available bovine serum. Upon addition of sulfide, the solution of 2 also showed very significant fluorescent intensity increases. The fluorescence was much stronger than in previously studied solvents. For example, the fluorescence intensity of DNS-Az (2) in response to 5 µM of sulfide in bovine serum was about 5-times of the intensity changes in buffer/Tween under identical conditions (due to the extremely strong fluorescence, all fluorescence spectra for bovine serum were recorded using a narrower slit width for both excitation and emission compared to other solvents). Though bovine serum showed background fluorescence (FIG. 4A, 0 s), it was negligible compared to the strong fluorescence of dansyl amide (3) generated from the reaction (FIG. 4). It should be noted that the reaction proceeded rapidly in bovine serum (complete within seconds, FIG. 4B). In contrast, it is interesting to note that the reaction was the slowest in buffer/Tween, which took about 3 min to complete (FIGS. 7A-7B).

An excellent linear relationship was also obtained in bovine calf serum in the sulfide concentration range of 1-100 µM (FIG. 3). The standard curve covers the range of reported endogenous levels of H$_2$S, indicating that this probe is very suitable for the detection of sulfide in biological samples. Overall, the results indicate that the anions and reducing agents normally encountered in the blood do not pose a problem in the quantitative detection of sulfide in a biological sample.

Figure 13:
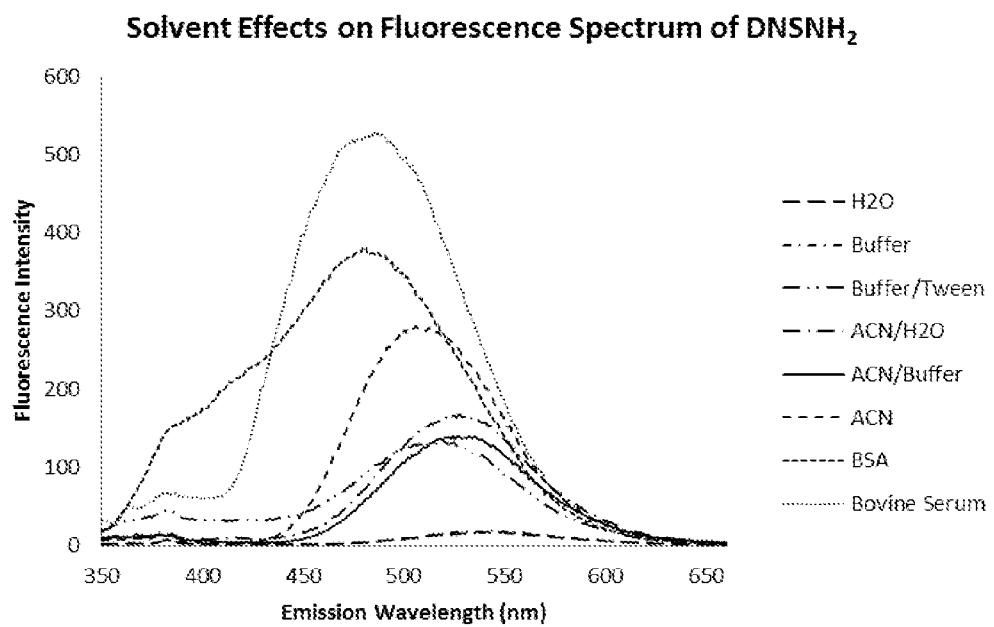
FIG. 13 is a graph showing fluorescence intensity (in arbitrary units) of DNS-NH$_2$ (5 μM) as a function of emission wavelength (nm) in various solvents (water, buffer, buffer/Tween, acetonitrile/water, acetonitrile/buffer, acetonitrile, BSA, and bovine serum). Both emission wavelength and fluorescence intensity are solvent dependent.

Additionally, the emission wavelength in bovine serum was shorter (493 nm) compared to the situation in buffer/acetonitrile (528 nm) and buffer/Tween (517 nm), most likely due to the solvatochromism of proteins present in the serum, which may lower the energy levels of the ground state of dansyl amide. As controls, we also studied the fluorescent properties of standard dansyl amide (3) in various solvents including bovine serum and found that indeed dansyl amide (3) exhibited different emission wavelengths depending on the solvent (FIG. 13). Such results are consistent with what was found with the tests using DNS-Az (2).

DNS-Az was also used in an in vitro assay to determine sulfide concentrations in blood. The sulfide concentration in mouse blood (C57BL6/J mouse model) was determined to be 31.9±9.4 µM. This value is consistent with previously reported values for the concentration of H$_2$S in mouse plasma obtained with the methylene blue colorimetric method (34.1 µM). Li, L., et al. *FASEB J.* 19:1196-1198 (2005). This proof-of-principle assay demonstrates the functionality of the chemosensors described herein for the detection and quantification of H$_2$S in biological samples.

In conclusion, dansyl azide proved to be a reduction-sensitive chemosensing agent for the detection and quantification of H$_2$S in aqueous solutions, including commercial bovine serum. The probe was found to be very selective for sulfide among 18 anions tested and other common reducing species, with a detection limit of 1 µM in buffer/Tween and 5 µM in bovine serum with a S/N ratio of 3:1. The linear relationship obtained in bovine serum covers the reported endogenous concentration range of H$_2$S. The simplicity and ease in measurements, which only requires addition of the probing molecule without any other reagents or further treatment, make this agent extremely easy to use. In addition, sulfide level in the biological system is tightly regulated and can experience rapid changes in concentration. The unprecedented fast response by DNS-Az (2) to sulfide allows it to be used for the detection of transient changes in sulfide levels. The probe, DNS-Az (2), is simple in structure, very easy to synthesize, and stable and amenable to long-term storage.

Unless defined otherwise, all technical and scientific terms used herein have the same meanings as commonly understood by one of skill in the art to which the disclosed invention belongs.

We claim:

1. A method of detecting hydrogen sulfide in a sample comprising contacting the sample with a chemosensing agent comprising an azide, wherein the chemosensing agent is represented by the following formula:

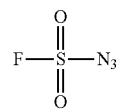

wherein

F is a fluorophore; and wherein the azide of the chemosensing agent is reduced by the hydrogen sulfide and the reduction of the azide elicits a change in the maximum emission wavelength of the chemosensing agent, the fluorescence quantum yield of the chemosensing agent, the shape of the emission spectra of the chemosensing agent, the fluorescence lifetime of the chemosensing agent, and combinations thereof.

2. The method of claim 1, wherein the fluorophore is selected from the group consisting of xanthene, xanthene derivatives, cyanine, cyanine derivatives, naphthalene, naphthalene derivatives, coumarin, coumarin derivatives, oxadiazole derivatives, pyrene, pyrene derivatives, oxazine derivatives, acridine, acridine derivatives, arylmethine derivatives, tetrapyrrole derivatives, fluorene, and fluorene derivative.

3. The method of claim 2, wherein the fluorophore is naphthalene or a naphthalene derivative.

4. The method of claim 1, wherein the chemosensing agent is defined by Formula I

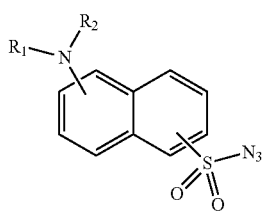

Formula I wherein

R$_1$ and R$_2$ are, independently, hydrogen, a substituted or unsubstituted alkyl group, a substituted or unsubstituted aryl group, or a substituted or unsubstituted heteroaryl group; or R$_1$ and R$_2$, together with the nitrogen atom to which they are attached, forms a 4- to 8-membered hetercyclic ring.

5. The method of claim 4, wherein R$_1$ and R$_2$ are both alkyl groups.

6. The method of claim 4, wherein R$_1$ is a phenyl group and R$_2$ is hydrogen.

7. The method of claim 1, wherein the chemosensing agent is defined by one of the following structures

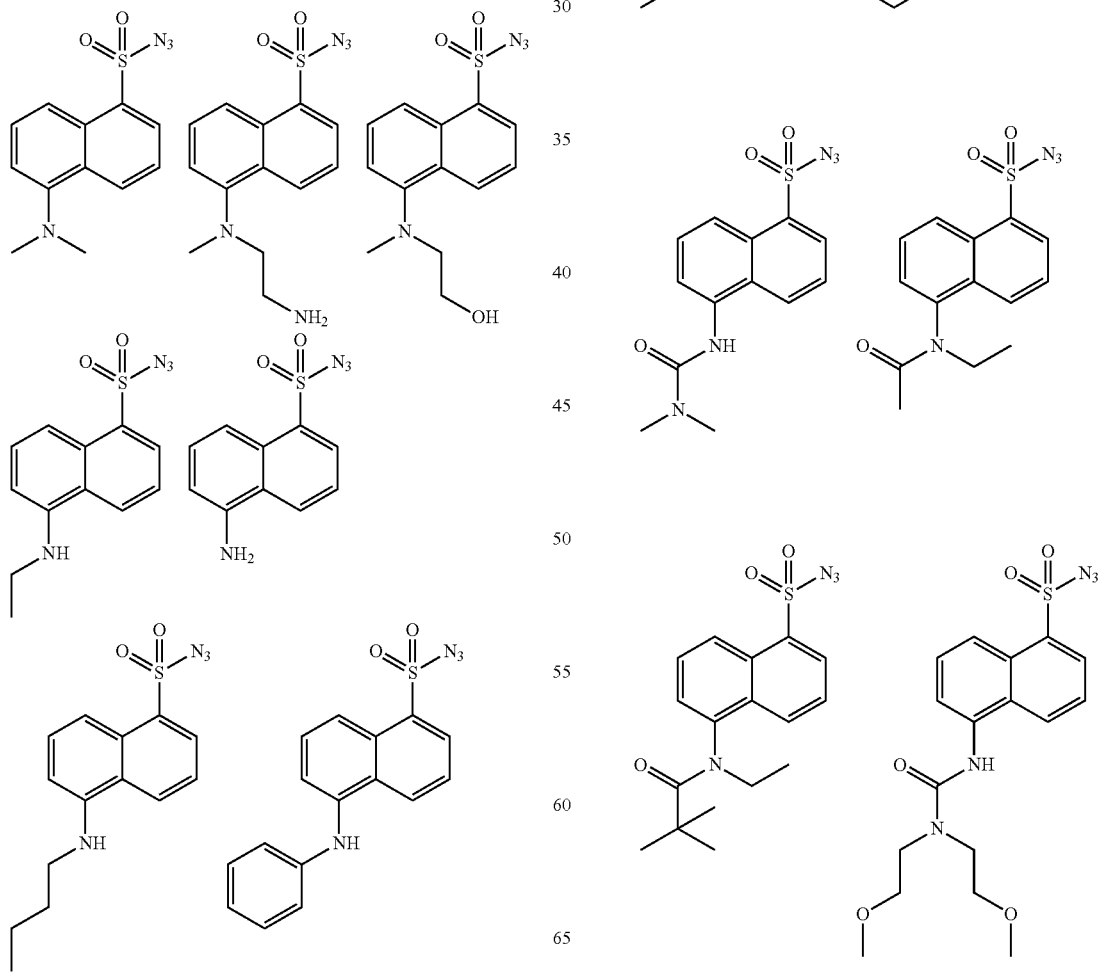

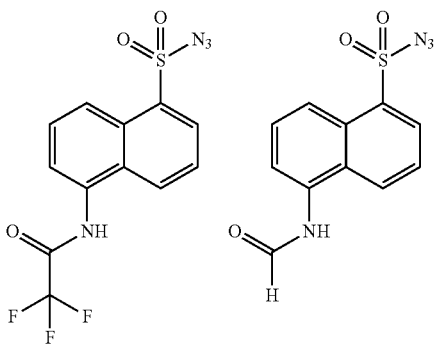

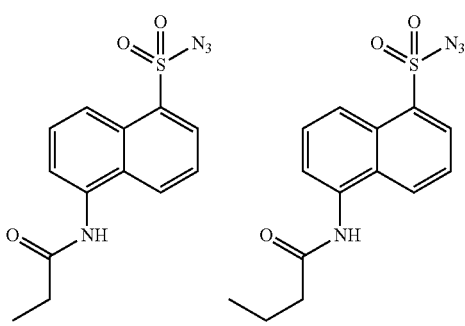

-continued

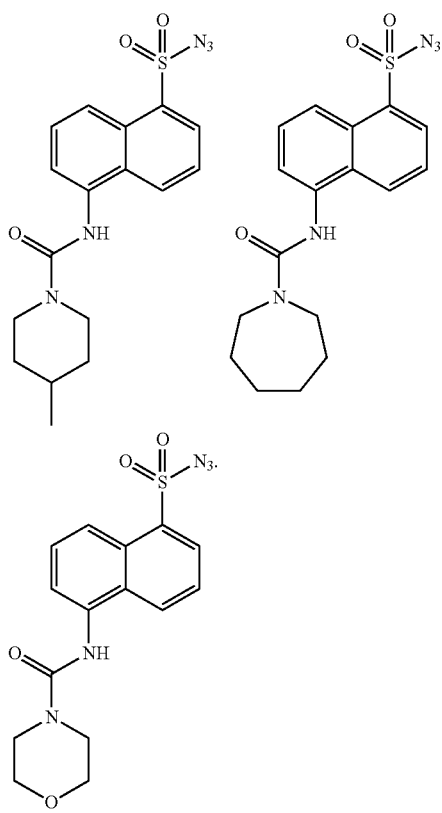

8. The method of claim 1, wherein the sample is an aqueous solution.

9. The method of claim 1, wherein the sample is a biological sample.

10. The method of claim 9, wherein the sample is a bodily fluid.

11. The method of claim 1, further comprising measuring the fluorescence of the chemosensing agent.

12. The method of claim 1, wherein the chemosensing agent reacts with the hydrogen sulfide without the addition of any additional reagents.

13. The method of claim 1, wherein the limit of detection for hydrogen sulfide is less than 100 μM.

14. The method of claim 11, wherein fluorescence intensity of the chemosensing agent, as measured at the maximum emission wavelength, reaches equilibrium less than ten minutes after contact with the hydrogen sulfide.

15. The method of claim 1, wherein the chemosensing agent is immobilized on a solid support.

16. A chemosensing agent represented by the following formula:

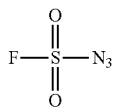

wherein F is a fluorophore, wherein the fluorophore is selected from the group consisting of xanthene, xanthene derivatives, cyanine, cyanine derivatives, naphthalene, coumarin, coumarin derivatives, oxadiazole derivatives, pyrene, pyrene derivatives, oxazine derivatives, acridine, acridine derivatives, arylmethine derivatives, tetrapyrrole derivatives, fluorene, and fluorene derivatives.

17. A chemosensing agent represented by Formula I:

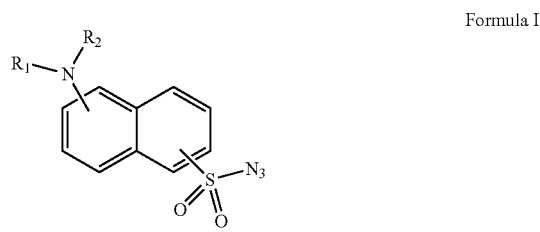

Formula I wherein,
(a) $R_1$ is hydrogen, a substituted or unsubstituted $C_2$-$C_{30}$ alkyl group, a substituted or unsubstituted aryl group, or a substituted or unsubstituted heteroaryl group, and $R_2$ is hydrogen, a substituted or unsubstituted $C_1$-$C_{30}$ alkyl group, a substituted or unsubstituted aryl group, or a substituted or unsubstituted heteroaryl group; or (b) $R_1$ and $R_2$, together with the nitrogen atom to which they are attached, form a 4- to 8-membered hetercyclic ring.

18. The chemosensing agent of claim 17, wherein $R_1$ and $R_2$ are both alkyl groups.

19. The chemosensing agent of claim 17, wherein the chemosensing agent is defined by one of the following structures:

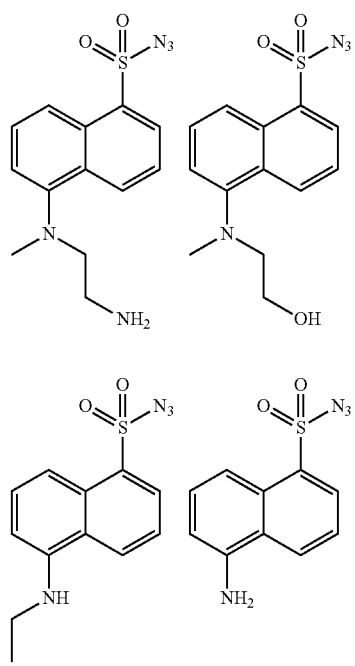

35
-continued
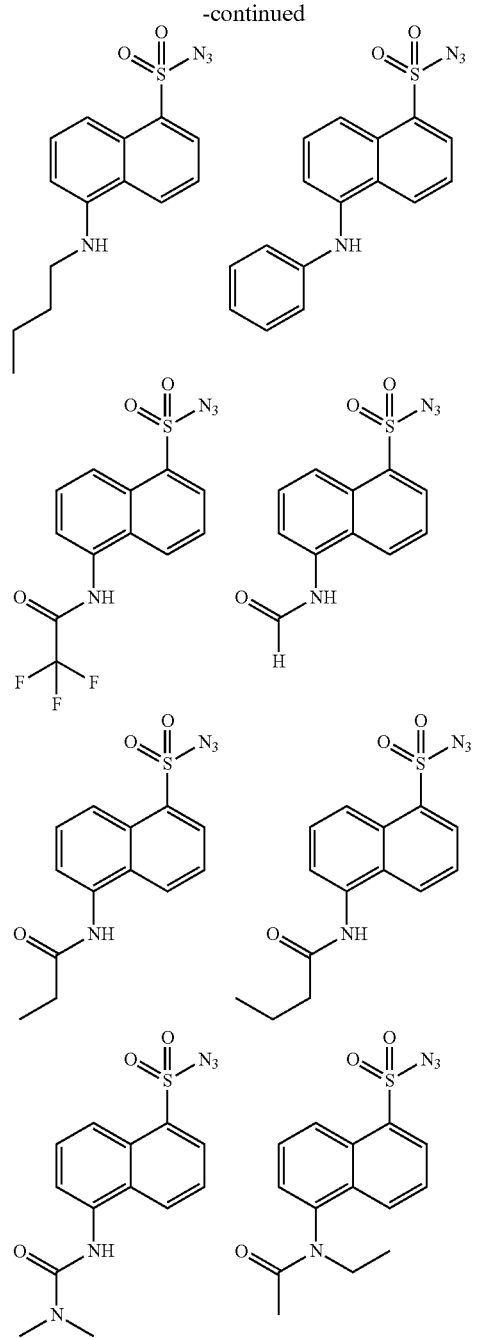
36
-continued
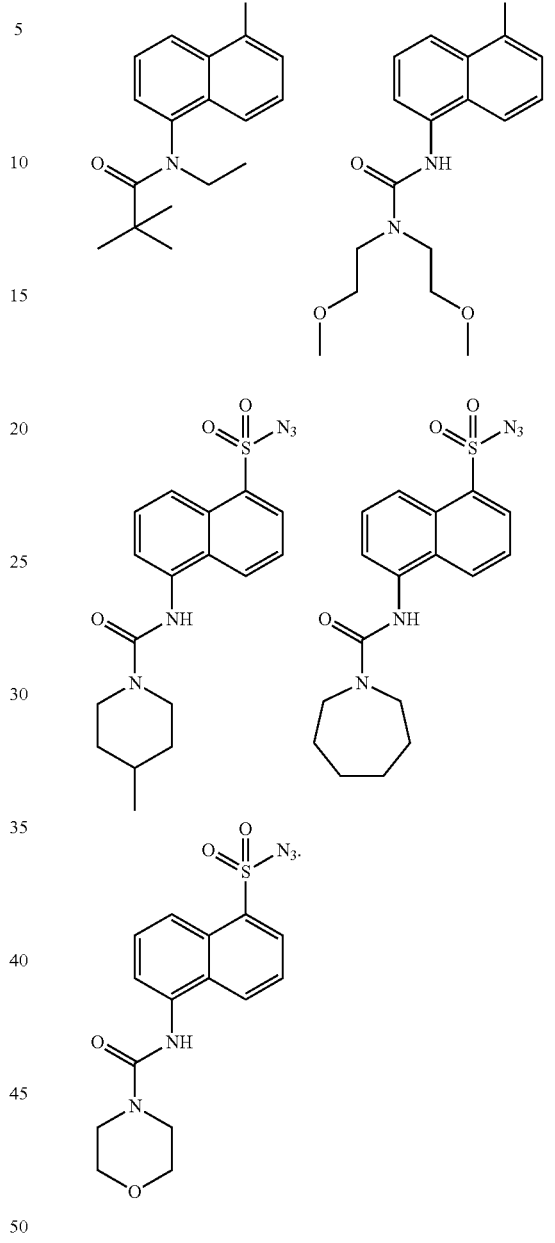
* * * * *

UNITED STATES PATENT AND TRADEMARK OFFICE
CERTIFICATE OF CORRECTION

| | | |
|---|---|---|
| PATENT NO. | : 9,175,165 B2 | Page 1 of 1 |
| APPLICATION NO. | : 13/997963 | |
| DATED | : November 3, 2015 | |
| INVENTOR(S) | : Hanjing Peng and Binghe Wang | |

It is certified that error appears in the above-identified patent and that said Letters Patent is hereby corrected as shown below:

In the specification

In column 1, following line 13, please add the following paragraph and heading:

--STATEMENT REGARDING FEDERALLY SPONSORED RESEARCH OR DEVELOPMENT

This invention was made with Government support under Grant No. GM084933 awarded by the National Institutes of Health. The Government has certain rights to the invention.--.

In the claims

In claim 4, column 31, line 19, please replace the term "hetercyclic" with "heterocyclic".

In claim 17, column 34, lines 31-32, please replace the term "hetercyclic" with "heterocyclic".

Signed and Sealed this
Ninth Day of August, 2016

Michelle K. Lee
*Director of the United States Patent and Trademark Office*